(12) United States Patent
Wiggins et al.

(10) Patent No.: US 9,037,430 B1
(45) Date of Patent: May 19, 2015

(54) METHODS AND SYSTEMS FOR NON-DESTRUCTIVELY TESTING A POLYCRYSTALLINE DIAMOND ELEMENT

(75) Inventors: Jason K. Wiggins, Draper, UT (US); Kenneth E. Bertagnolli, Riverton, UT (US); Gene Bogdanov, Manchester, CT (US); Reinhold Ludwig, Paxton, MA (US)

(73) Assignee: US SYNTHETIC CORPORATION, Orem, UT (US)

( * ) Notice: Subject to any disclaimer, the term of this patent is extended or adjusted under 35 U.S.C. 154(b) by 1083 days.

(21) Appl. No.: 12/830,878

(22) Filed: Jul. 6, 2010

Related U.S. Application Data

(60) Provisional application No. 61/223,581, filed on Jul. 7, 2009.

(51) Int. Cl.
*G01R 27/00* (2006.01)
*G06F 19/00* (2011.01)

(52) U.S. Cl.
CPC ...................... *G06F 19/00* (2013.01)

(58) Field of Classification Search
CPC ............... B24D 3/06; B24D 3/08; B24D 3/10
USPC ............................. 702/35, 57, 65, 81; 423/446
See application file for complete search history.

(56) References Cited

U.S. PATENT DOCUMENTS 5,588,429 A * 12/1996 Isaacson et al. ............... 600/547
6,265,884 B1 * 7/2001 Menashi et al. ............... 324/717
6,858,080 B2 * 2/2005 Linares et al. ................. 117/86
6,878,447 B2   4/2005 Griffin et al.
7,866,418 B2 * 1/2011 Bertagnolli et al. ........ 175/420.2

OTHER PUBLICATIONS

Bogdanov, G., et al., Non-Destructive Testing of Polycrystalline Diamond Cutters Using DC Electrical Conductivity Imaging, Meas.Sci. Technol 20 (2009) (10 pages).
U.S. Appl. No. 61/223,581, filed Jul. 7, 2009, Wiggins et al.
Adler et al. "Uses and abuses of EIDORS: an extensible software base for EIT" Institute of Physics Publishing, Physiol. Meas. 27 (2006) S25-S42.
Borcea "Electrical impedance tomography" Institute of Physics Publishing, Inverse Problems 18 (2002) R99-R136.

(Continued)

*Primary Examiner* — Elias Desta
(74) *Attorney, Agent, or Firm* — Dorsey & Whitney LLP

(57) ABSTRACT

Embodiments of the invention relate to electrical impedance tomography testing systems and methods for non-destructively testing a polycrystalline diamond element (e.g., a polycrystalline diamond table of a polycrystalline diamond compact or a freestanding polycrystalline diamond table) using electrical impedance tomography to locate one or more high-electrical-conductivity regions (e.g., one or more regions of poorly sintered diamond crystals and/or high-metal-solvent catalyst content) and/or one or more low-electrical-conductivity regions (e.g., porosity and/or cracks) in the tested polycrystalline diamond element. Further embodiments relate to a rotary drill bit including at least one polycrystalline diamond compact that has been selectively positioned so that one or more high-electrical-conductivity regions of a polycrystalline diamond table thereof identified using the non-destructive testing systems and methods disclosed herein are not positioned to engage a subterranean formation during drilling.

11 Claims, 19 Drawing Sheets

(56) References Cited

OTHER PUBLICATIONS

Brown "Medical impedance tomography and process impedance tomography: a brief review" Institute of Physics Publishing, Meas. Sci. Technol. 12 (2001) 991-996.

Cheney et al. "Electrical Impedance Tomography" SIAM Review, vol. 41, No. 1, pp. 85-101, Jan. 22, 1999.

Dahlin "The development of DC resistivity imaging techniques" Computers & Geosciences 27 (2001) 1019-1029.

Dijkstra et al. "Review Clinical applications of electrical impedance tomography" Journal of Medical Engineering & Technology, vol. 17, No. 3 (May/Jun. 1993) pp. 89-98.

Gilmore "Idustrial ultrasonic imaging and microscopy" J. Phys. D: Appl. Phys. 29 (1996) 1389-1417.

Lammer "Mechanical properties of polycrystalline diamonds" Materials Science and Technology, Nov. 1988, vol. 4, pp. 949-955.

Li et al. "Sintering behaviour of the diamond-super invar alloy system at high temperature and pressure" Journal of Materials Science 25 (1990) 4150-4156.

Lionheart "EIT reconstruction algorithms: pitfalls, challenges and recent developments" Institute of Physics Publishing, Physiol. Meas. 25 (2004) 125-142.

Loke et al. "Practical techniques for 3D resistivity surveys and data inversion" Geophysical Prospecting, 1996, 44, 499-523.

Loke et al. "Rapid least-squares inversion of apparent resistivity pseudosections by a quasi-Newton method" Geophysical Prospecting, 1996, 44, 131-152.

Loke "Tutorial: 2-D and 3-D electrical imaging surveys" Online: http://www.geoelectrical.com/coursenotes.zip Apr. 2001.

Loke "Tutorial: 2-D and 3-D electrical imaging surveys" Online: http://www.geoelectrical.com/coursenotes.zip Sep. 2002.

Loke "Tutorial: 2-D and 3-D electrical imaging surveys" Online: http://www.geoelectrical.com/coursenotes.zip Jul. 2004.

Miess et al. "Fracture toughness and thermal resistance of polycrystalline diamond compacts" Materials Science and Engineering A209 (1996) 270-276.

Ohno et al. "Cost reduction of polycrystalline diamond compact bits through improved durability" Geothermics 31 (2002) 245-262.

Pain et al. "Effective multidimensional resistivity inversion using finite-element techniques" Geophys. J. Int. (2002) 151, 710-728.

Tapp et al. "Chemical engineering applications of electrical process tomography" Sensors and Actuators B 92 (2003) pp. 17-24.

Wentorf et al. "Sintered Superhard Materials" Science, vol. 208, pp. 872-880, 1980.

York "Status of electrical tomography in industrial applications" Journal of Electronic Imaging 10(3), 608-619 (Jul. 2001).

* cited by examiner

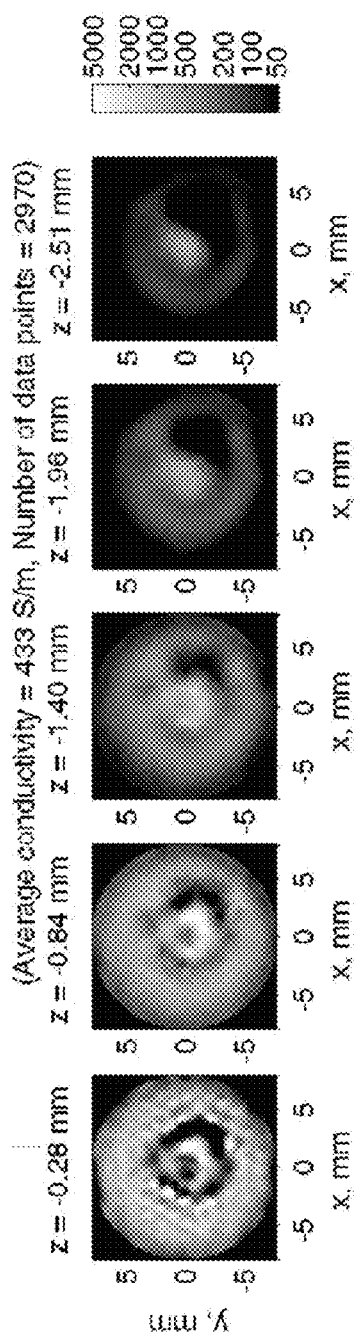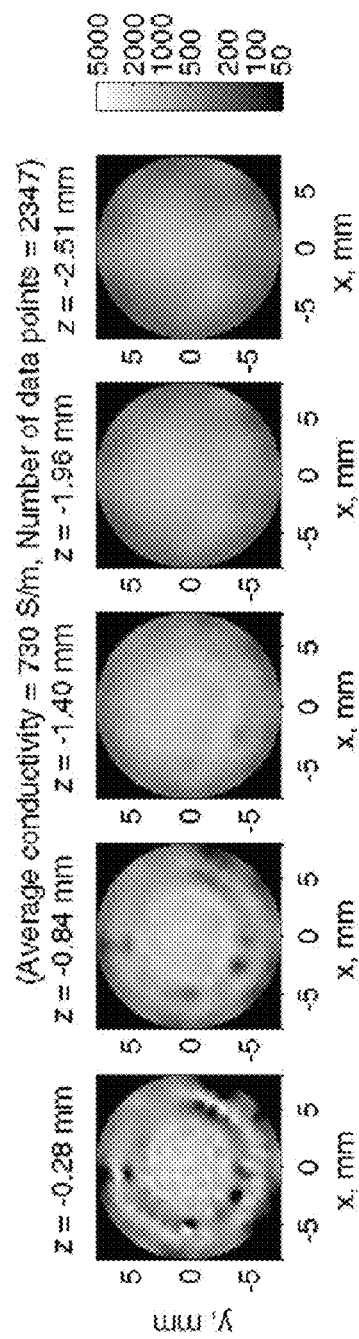
*Fig. 9A*    *Fig. 9B*

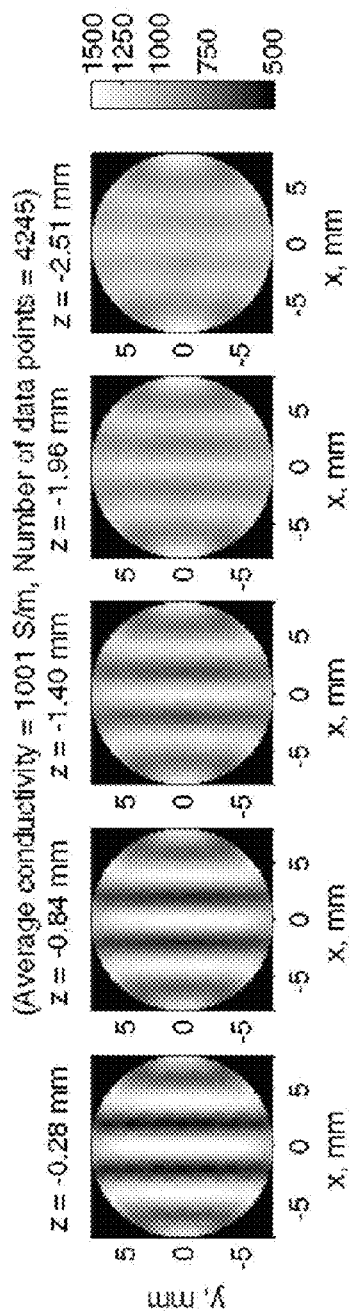
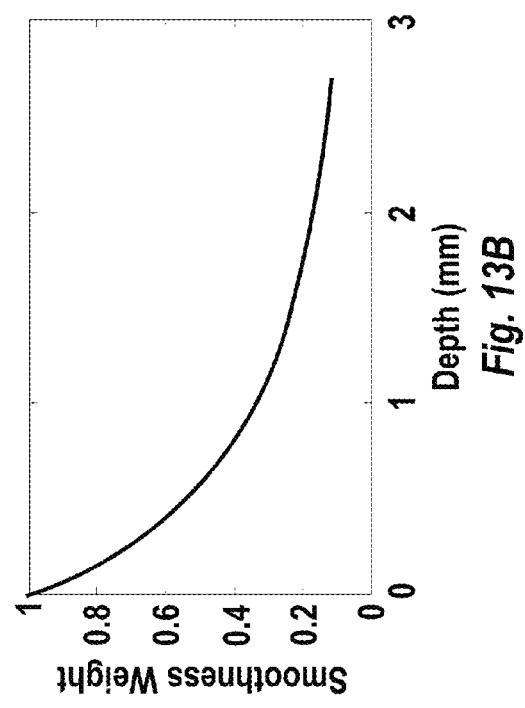
Fig. 13A
Fig. 13B

METHODS AND SYSTEMS FOR NON-DESTRUCTIVELY TESTING A POLYCRYSTALLINE DIAMOND ELEMENT

CROSS-REFERENCE TO RELATED APPLICATION

This application claims the benefit of U.S. Provisional Application No. 61/223,581 filed on 7 Jul. 2009, the disclosure of which is incorporated herein, in its entirety, by this reference.

BACKGROUND

Wear-resistant, polycrystalline diamond compacts ("PDCs") are utilized in a variety of mechanical applications. For example, PDCs are used in drilling tools (e.g., cutting elements, gage trimmers, etc.), machining equipment, bearing apparatuses, wire-drawing machinery, and in other mechanical apparatuses.

PDCs have found particular utility as superabrasive cutting elements in rotary drill bits, such as roller-cone drill bits and fixed-cutter drill bits. A PDC cutting element typically includes a superabrasive polycrystalline diamond ("PCD") layer commonly known as a diamond table or a PCD table. The PCD table is formed and bonded to a cemented tungsten carbide substrate using a high-pressure/high-temperature ("HPHT") process.

The PDC cutting element may be brazed directly into a preformed pocket, socket, or other receptacle formed in a bit body. The substrate may often be brazed or otherwise joined to an attachment member, such as a cylindrical backing. A rotary drill bit typically includes a number of PDC cutting elements affixed to the bit body. A stud carrying the PDC may also be used as a PDC cutting element when mounted to a bit body of a rotary drill bit by press-fitting, brazing, or otherwise securing the stud into a receptacle formed in the bit body.

The performance of PDCs has been improving over the years as manufacturing technology advances. However, there can be some variability in any manufacturing process that results in varying PDC durability from the same production batch.

Very few non-destructive testing ("NDT") methods have been effective for testing PDCs. X-ray imaging is not effective due to strong X-ray attenuation of the cemented tungsten carbide substrate. Ultrasonic imaging can achieve high resolution, but the observed features may have little relationship to the properties that the manufacturer would be interested in measuring in the PDC. Eddy current measurements may have low resolution and excessive requirements for sensor positioning precision. Also, the utility of eddy current testing may be limited because the PCD table and substrate of the PDC are often ferromagnetic. Infrared imaging has so far achieved useful contrast only at temperatures high enough to damage the PCD table.

SUMMARY

Embodiments of the invention relate to systems and methods for non-destructively testing a PCD element (e.g., a PCD table of a PDC or a freestanding PCD table) using electrical impedance tomography ("EIT") so that one or more defects in the PCD element may be identified, which are characterized by being one or more high-electrical-conductivity regions and/or one or more low-electrical-conductivity regions in the PCD element. Such high-electrical-conductivity regions may be regions of poorly sintered diamond crystals, high metal-solvent catalyst content regions, other flaws, or combinations of the foregoing. Such low-electrical-conductivity regions may be regions of porosity and/or cracks. Other embodiments relate to a rotary drill bit including at least one PDC that has been selectively oriented so that one or more defects of a PCD table thereof identified using the non-destructive testing systems and methods disclosed herein are not positioned to engage a subterranean formation during drilling.

In an embodiment, a method of non-destructively testing a PCD element includes measuring electrical resistance at a plurality of locations of the PCD element. The method further includes calculating an electrical conductivity distribution for the PCD element at least partially based on the measured electrical resistance. The method may further include analyzing the electrical conductivity distribution to determine if one or more defects are present in the PCD element.

In an embodiment, a method of selectively orienting and mounting a PCD table of a PDC on a drill bit body is disclosed. The method includes measuring electrical resistance at a plurality of locations of a PCD table of the PDC, and calculating an electrical conductivity distribution for the PCD table at least partially based on the measured electrical resistance. The method further includes analyzing the electrical conductivity distribution to locate one or more defects in the PCD table, and mounting the PDC on the bit body so that the one or more defects of the PCD table thereof are not oriented as a cutting region that engages a subterranean formation during drilling.

In an embodiment, a rotary drill bit is disclosed. The rotary drill bit includes a bit body configured to engage a subterranean formation, and a plurality of polycrystalline diamond cutters mounted to the bit body. At least one polycrystalline diamond cutter of the plurality of polycrystalline diamond cutters includes a PCD table having one or more defects therein. The at least polycrystalline diamond cutter is oriented on the bit body so that the one or more defects thereof are not positioned as a cutting region that engages the subterranean formation during drilling.

In an embodiment, a method of selectively orienting and mounting a PDC on a test fixture is disclosed. The method includes measuring electrical resistance at a plurality of locations of a PCD table of a PDC, and calculating an electrical conductivity distribution for the PCD table at least partially based on the measured electrical resistance. The method further includes analyzing the electrical conductivity distribution to locate one or more defects in the PCD table. The method additionally includes mounting the PDC on the test fixture so that the one or more defects of the PCD table thereof are not positioned as a cutting region that can engage a test workpiece.

In an embodiment, an EIT testing system is disclosed for non-destructively testing a PCD element. The EIT testing system includes an EIT unit configured to measure an electrical resistance of the PCD element at a plurality of locations thereof. The EIT testing system further includes a computer coupled to the EIT unit. The computer is configured to calculate an electrical conductivity distribution for the PCD element at least partially based on the measured electrical resistance, analyze the electrical conductivity distribution to determine if one or more defects are present in the polycrystalline diamond element, and determine one or more of a type of, a number of, a size of, or a position of defects in the polycrystalline diamond element at least partially based on the electrical conductivity distribution. In some embodiments, the computer may further be configured to determine whether to accept or reject the polycrystalline diamond element at least partially based on the electrical conductivity distribution.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the invention, wherein identical reference numerals refer to identical elements or features in different views or embodiments shown in the drawings.

FIGS. 9A and 9B are electrical conductivity images from PCD tables of two different PDC cutter samples having ring-like zones of poor metal-solvent catalyst penetration.

FIGS. 13A and 13B illustrate the effect of adjusted smoothness constraint at 4 mm period resolution test and when smoothness weighing is used, respectively.

DETAILED DESCRIPTION

I. Overview

Figure 1:
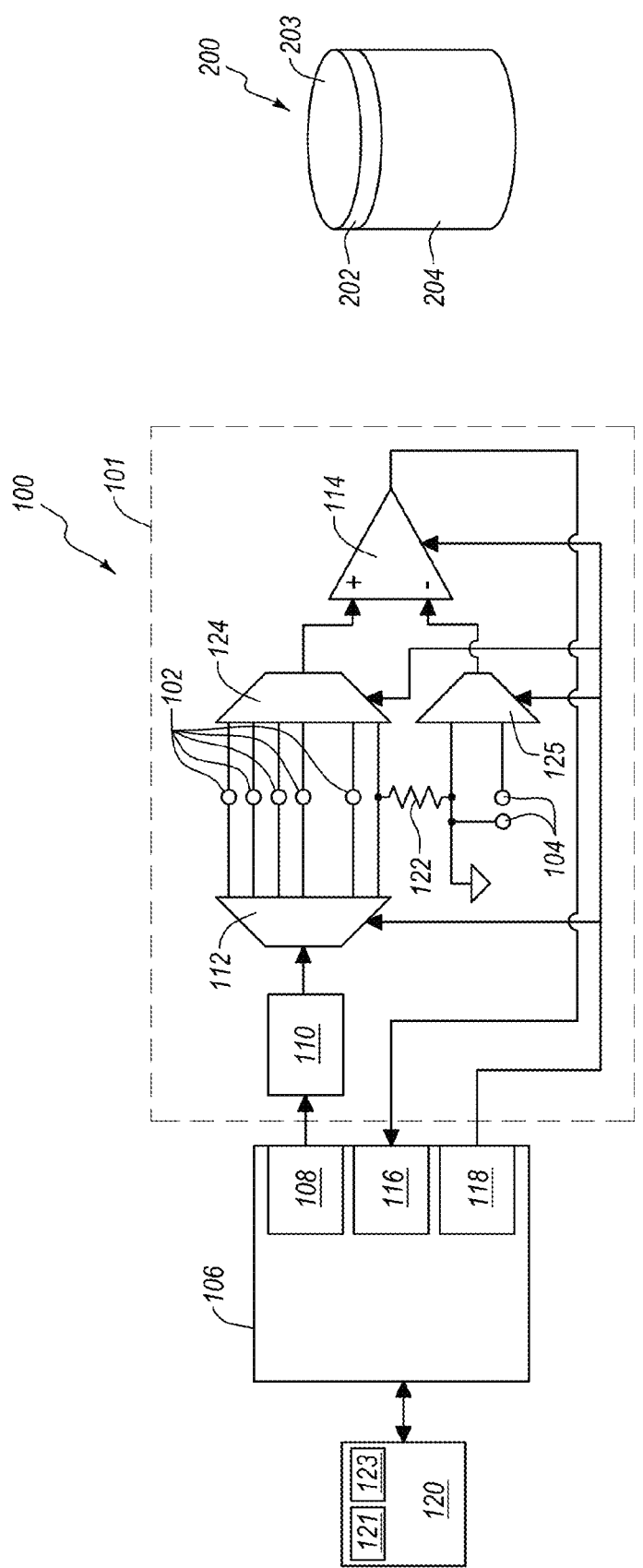
FIG. 1 is a functional block diagram of an embodiment of a multi-probe resistance measurement EIT testing system configured to non-destructively test PDC samples.

Embodiments of the invention relate to systems and methods for non-destructively testing a PCD element (e.g., a PCD table of a PDC or a freestanding PCD table) using electrical impedance tomography ("EIT") so that one or more defects in the PCD element may be identified, which are characterized by being one or more high-electrical-conductivity regions and/or one or more low-electrical-conductivity regions in the PCD element. The local electrical conductivity in a PCD element may be indicative of local metal-solvent catalyst content within the PCD element. Other embodiments relate to a rotary drill bit including at least one PDC that has been selectively positioned so that one or more defects of a PCD table thereof identified using the non-destructive testing systems and methods disclosed herein are not positioned to engage a subterranean formation during drilling.

The PCD elements capable of being tested using the systems and methods disclosed herein include PCD tables of one-step and two-step PDCs and freestanding PCD tables. A one-step PDC may include a PCD table integrally formed and bonded to a cemented carbide substrate. The PCD table includes directly bonded-together diamond crystals exhibiting diamond-to-diamond bonding (e.g., $sp^3$ bonding) therebetween that define a plurality of interstitial regions. A metal-solvent catalyst (e.g., iron, nickel, cobalt, or alloys thereof) is disposed in at least a portion of the interstitial regions. The cemented carbide substrate may comprise tungsten carbide, tantalum carbide, vanadium carbide, niobium carbide, chromium carbide, titanium carbide, or combinations of the foregoing carbides cemented with iron, nickel, cobalt, or alloys of the foregoing metals. For example, the cemented carbide substrate may comprise cobalt-cemented tungsten carbide.

Generally, a one-step PDC may be formed by placing un-bonded diamond crystals adjacent to a cemented carbide substrate and subjecting the diamond crystals and the cemented carbide substrate to an HPHT process under diamond stable HPHT conditions. During the HPHT process, metal-solvent catalyst from the cemented carbide substrate at least partially melts and sweeps into interstitial regions between the diamond crystals to catalyze growth of diamond and formation of diamond-to-diamond bonding between adjacent diamond crystals so that a PCD table is formed that bonds to the cemented carbide substrate upon cooling from the HPHT process.

A two-step PDC may also be formed in which an at least partially leached PCD table (i.e., a freestanding PCD table) may be placed adjacent to a cemented carbide substrate and subjected to an HPHT process under diamond stable conditions. During the HPHT process, an infiltrant from the cemented carbide substrate infiltrates into the interstitial regions of the at least partially leached PCD table and bonds the infiltrated PCD table to the cemented carbide substrate upon cooling from the HPHT process.

The at least partially leached PCD table may be formed by separating the PCD table from a one-step PDC by removing the cemented carbide substrate via grinding, machining, or combinations thereof and leaching the metal-solvent catalyst from separated PCD table in a suitable acid. The at least partially leached PCD table may also be formed by other methods, such as sintering diamond particles in the presence of a metal-solvent catalyst to form a PCD table or disk and leaching the PCD table in an acid.

Both one-step and two-step PDCs may be subjected to a leaching process to remove a portion of the metal-solvent catalyst or infiltrant from the PCD table to a selected depth and from one or more exterior surfaces. Removal of the metal-solvent catalyst or infiltrant may help improve thermal stability and/or wear resistance of the PCD table.

Although diamond is not electrically conductive by itself, the sintering process for fabricating PCD introduces small amounts of metal-solvent catalyst (e.g., iron, nickel, cobalt, or alloys thereof) into the interstitial regions between the bonded diamond crystals of the PCD. For example, cobalt is molten during sintering of diamond crystals, and acts as a solvent catalyst that promotes diamond-to-diamond crystal bonding between the diamond crystals during the HPHT sintering process. The macroscopic electrical conductivity of PCD may be closely related to the metal-solvent catalyst content therein and/or diamond-to-diamond crystal sintering quality.

Metal-solvent catalyst content in a PCD table may correlate with degradation of certain mechanical properties of the PCD table. For example, higher metal-solvent content correlates with lower thermal resilience, which is a property relevant to subterranean drilling applications. The primary mechanisms for metal-solvent catalyst content contributing to PDC degradation are currently believed to be diamond-metal differential thermal expansion and diamond graphitization at higher temperatures. Metal-solvent catalyst content in PCD is such a problem that a portion of the metal-solvent catalyst is often leached from the PCD table to a selected depth of about 20 µm to about 500 µm as a standard manufacturing step. Fracture toughness is mostly believed to be a function of grain size, with larger grain size correlating with a higher fracture toughness. Metal-solvent catalyst content may decrease in a PCD table with increasing diamond-crystal grain size provided that other process conditions remain the same. Grain size is easier to control in a manufacturing process, as it is closely tied to the diamond feed particle size, whereas metal-solvent catalyst content also depends on local pressure during sintering and/or diamond surface chemistry, which may be subject to greater variation. Localized lower pressure and/or diamond surface contamination causes poorer bonding between diamond crystals and increased metal-solvent catalyst content. These poor sinter zones are detectable in EIT electrical conductivity images as one or more high-electrical-conductivity regions.

The one or more high-electrical-conductivity regions exhibit an electrical conductivity that is greater than an average electrical conductivity of the entire PCD table of the PDC. The one or more high-electrical-conductivity regions may exhibit a maximum linear cross-sectional dimension (e.g., a maximum diameter or other maximum linear dimension) of at least about 0.25 mm, about 0.5 mm to about 4 mm, about 1 mm to about 3 mm, about 1 mm to about 2 mm, or about 0.75 mm to about 1.75 mm. In some embodiments, the one or more high-electrical-conductivity regions may cover more than about 10% of an exterior surface of the PCD table, such as about 10% to about 50%, about 10% to about 25%, or about 25% to about 50%. Thus, an individual one of the high-electrical-conductivity regions may be comprised of a plurality of bonded-together diamond crystals having metal-solvent catalyst disposed in interstitial regions between the bonded diamond crystals. The one or more high-electrical-conductivity regions may have an average electrical conductivity of at least about 1.5 to about 10 times greater than the average electrical conductivity of the entire PCD table, such as about 1.5 to about 5 times, about 2 to about 6 times, or about 2.5 to about 4 times. Generally, the average electrical conductivity of the entire PCD table may be about 2,000 S/m to about 5,000 S/m and the average electrical conductivity of the one or more high-electrical-conductivity regions may be about 3,000 to about 50,000 S/m. For example, the average electrical conductivity of the entire PCD table may be about 2,500 S/m and the average electrical conductivity of the one or more high-electrical-conductivity regions may be about 4,000 S/m, the average electrical conductivity of the entire PCD table may be about 3,000 S/m to about 5,000 S/m and the average electrical conductivity of the one or more high-electrical-conductivity regions may be about 4,500 S/m to about 9,000 S/m, or the average electrical conductivity of the entire PCD table may be about 4,000 S/m to about 4,500 S/m and the average electrical conductivity of the one or more high-electrical-conductivity regions may be about 10,000 S/m to about 15,000 S/m. In another example, the entire PCD table may exhibit an average electrical conductivity of about 3,000 to about 5,000 S/m and the one or more high-electrical-conductivity regions may exhibit an average electrical conductivity of about 6,000 to about 10,000 S/m, the average electrical conductivity of the entire PCD table may be about 4,000 to about 5,000 S/m and the average electrical conductivity of the one or more high-electrical-conductivity regions may be about 8,000 to about 10,000 S/m, the average electrical conductivity of the entire PCD table may be about 2,000 to about 4,000 S/m and the average electrical conductivity of the one or more high-electrical-conductivity regions may be about 3,500 to about 8,000 S/m.

Additives to the PCD table may also influence the electrical conductivity thereof. For example, the PCD table may include silicon, silicon carbide, graphite, tungsten, tungsten carbide, boron, combinations thereof, or other selected constituents. Some additives may be alloyed with the metal-solvent catalyst of the PCD table that is present interstitially between bonded diamond crystals. For example, cobalt may be alloyed with tungsten and/or boron.

Regions of low electrical conductivity are also detectable in EIT electrical conductivity images as one or more low-electrical-conductivity regions, such as porosity and/or cracks. The one or more low-electrical-conductivity regions exhibit an electrical conductivity that is less than an average electrical conductivity of the entire PCD table of the PDC.

II. EIT Testing System Embodiments

FIG. 1 is a functional block diagram of an embodiment of a multi-probe resistance measurement EIT testing system 100 configured to non-destructively test PDC samples. A representative PDC sample 200 is illustrated with a PCD table 202 bonded to a cemented carbide substrate 204. The system 100 includes an EIT unit 101 configured to measure an electrical resistance of the PCD 202 at a plurality of locations. The EIT unit 101 may include a plurality of probes 102 (e.g., 121 spring-loaded probes) configured to electrically contact a surface 203 of the PCD table 202 of the PDC sample 200, and a plurality of probes 104 (e.g., two probes) to contact the substrate 204 of the PDC sample 200. For example, the probes 102 may be spring-loaded pins (e.g., "pogo" pins used in printed circuit board testing) that make contact with the surface 203 of the PCD table 202. In an embodiment, for a cylindrical PDC sample 200 having a 16 mm diameter, up to 7260 linearly-independent 4-probe resistance measurements may be acquired and recorded at a plurality of different locations when 121 of the probes 102 and the probes 104 are used in the system 100. It is noted that more probes may be used for a larger PDC sample. As will be discussed in more detail hereinbelow, the electrical resistance measurements may then be reconstructed into a 3D electrical conductivity distribution of the PCD table 202 using a reconstruction algorithm.

Figure 2:
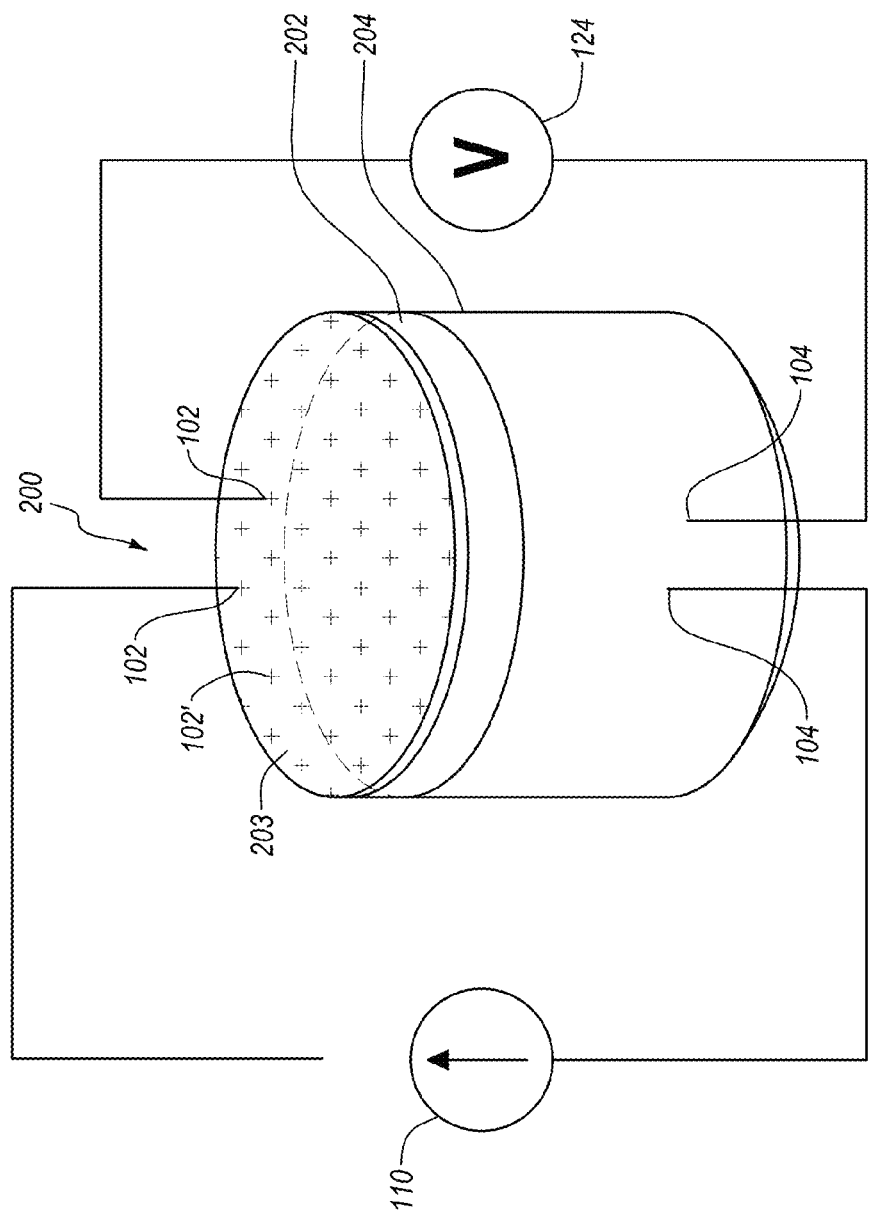
FIG. 2 is a schematic diagram for four-probe resistance measurements on a PDC sample using the system shown in FIG. 1.

The system 100 is configured to make 4-probe DC resistance measurements in the approximate range from 0.1 mΩ to 1Ω on the PDC sample 200. The substrate 204 of the PDC sample 200 may be used as a reference conductor. One of the current probes and one of the voltage probes may be electrically connected to the substrate 204. The 4-probe measurement setup is completed by multiplexing one of the top surface-contacting probes 102 for current injection and another one of the top surface-contacting probes 102 for voltage measurement. Probe locations for the probes 102 are shown in the schematic diagram of FIG. 2 as star shapes and only one location is labeled as 102' for sake of clarity. Using this probe arrangement, only one large current multiplexer and one large voltage multiplexer are required instead of two of each for a fully flexible 4-probe setup. The useful 4-probe measurements are linear combinations of the measurements acquired with the 2-multiplexer instrument. Using full 4-probe multiplexing adds little additional information to the reconstruction problem aside from some noise averaging.

Referring again to FIG. 1, the system 100 includes a data acquisition module 106 (e.g., a USB data acquisition) coupled to the EIT unit 101. The data acquisition module 106 includes an analog output 108 that controls the output current of a precision current source 110 in the range from about −150 mA to about +150 mA. The current is routed to one of the 121 sensor probes 102 in contact with the PCD table 202 through a 1:128 current multiplexer 112. For example, the current multiplexer 112 may be built using commercially available 8:1 analog multiplexers with 5Ω maximum series 'on' resistance. One of the reference probes 104 contacting the substrate 204 serves as a current sink and is grounded. A respective voltage measurement is taken between the sensor probe 102 selected by the 128:1 voltage multiplexer 124 and the second reference probe 104 contacting the substrate. The voltage is amplified by a programmable-gain instrumentation amplifier 114 and sent to an analog input 116 of the data acquisition module 106. The amplifier 114 may be programmed for gains of, for example, about 1, about 250, about 1000, and about 4000. Unity gain may be used for probe contact resistance measurement. Simple RC filters may be installed in the analog path to band-limit noise. A plurality of digital outputs 118 (e.g., 18 total) from the data acquisition module 106 control all the multiplexers and the amplifier gain of the amplifier 124.

A computer 120 (e.g., a desktop computer) is coupled to or includes the data acquisition module 106 therein. The computer 120 receives the electrical resistance measurements taken by the EIT unit 101 from the analog input 116 of the data acquisition module 106. The computer 120 includes memory 121 storing software thereon containing computer executable instructions configured for reconstructing/calculating/analyzing the electrical conductivity distribution in the PCD table 202 of the PDC sample 200 being tested in accordance with a reconstruction algorithm discussed in more detail hereinbelow and one or more processors 123 for executing the computer executable instructions. For example, the one or more processors 123 may control the data acquisition module 106 and process the measured resistance data to reconstruct and analyze the electrical conductivity distribution. The computer executable instructions are instructions for the one or more processors 123 to execute all or part of the inventive methods disclosed herein and further described hereinbelow with respect to FIGS. 14-16.

To calibrate the instrument, one or more precision reference resistors 122 are provided, such as 50 mΩ, 20 mΩ and 10 mΩ in an embodiment. A secondary 4:1 voltage multiplexer 125 may be provided to accommodate 4-wire measurements of these reference resistors 122. FIG. 1 shows only one exemplary reference resistor, but the connections of the other reference resistors may be similar.

Figure 3:
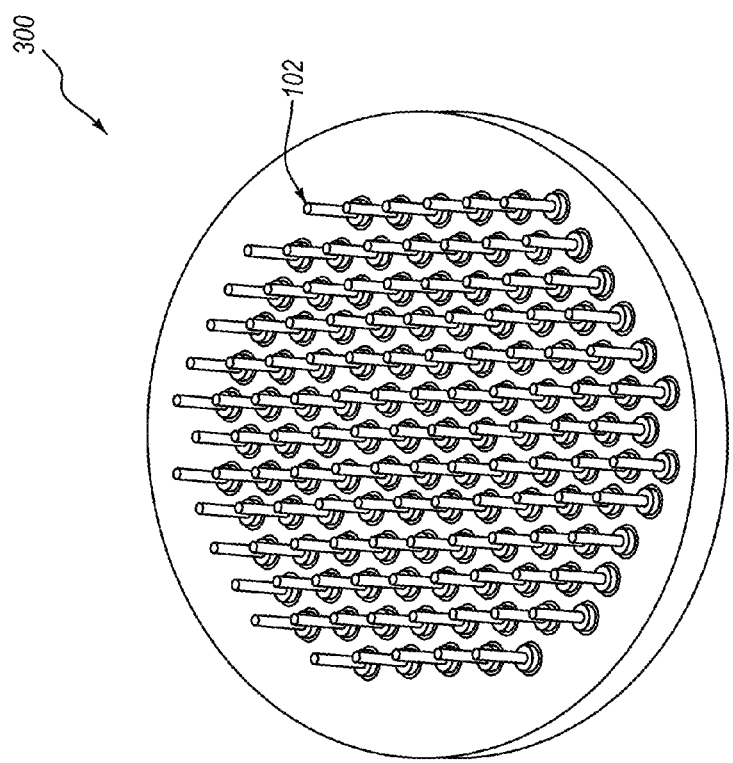
FIG. 3 is a top isometric view of the sensor-probe arrangement of the testing system shown in FIG. 2.

Referring to FIG. 3, an embodiment for a sensor assembly 300 of the EIT unit 101 includes the plurality of probes 102 is illustrated. In an embodiment, the probes 102 may be arranged in a triangular-grid pattern having a center-to-center spacing of about 0.050 in (1.3 mm) to achieve the maximum probe density for the given spacing. In such an embodiment, the sensor assembly 400 is designed for a 0.625 in (15.9 mm) diameter PDC sample, and contains 121 spring-loaded pins. The probe spacing was selected as a compromise between imaging resolution and hardware complexity. To minimize the errors introduced into the measurements by deviations of pin landing coordinates from their nominal values, the actual landing coordinates may be measured from an image acquired by an optical scanner. It should be noted that other sensor-assembly configurations may be used for PDC samples having a different size and/or a different configuration.

Figure 4A:
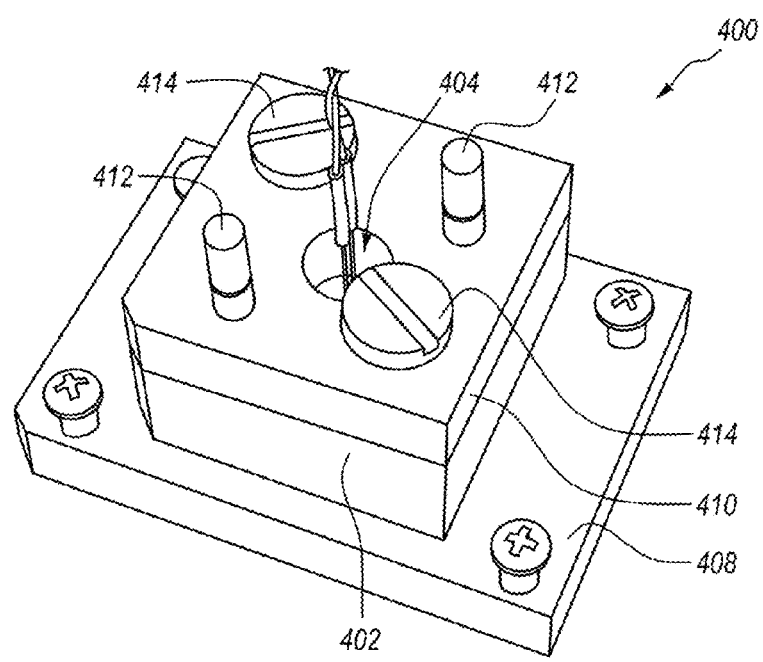
FIG. 4A is an isometric view of an embodiment of a sample-holder assembly for holding a PDC sample to be tested.
Figure 4B:
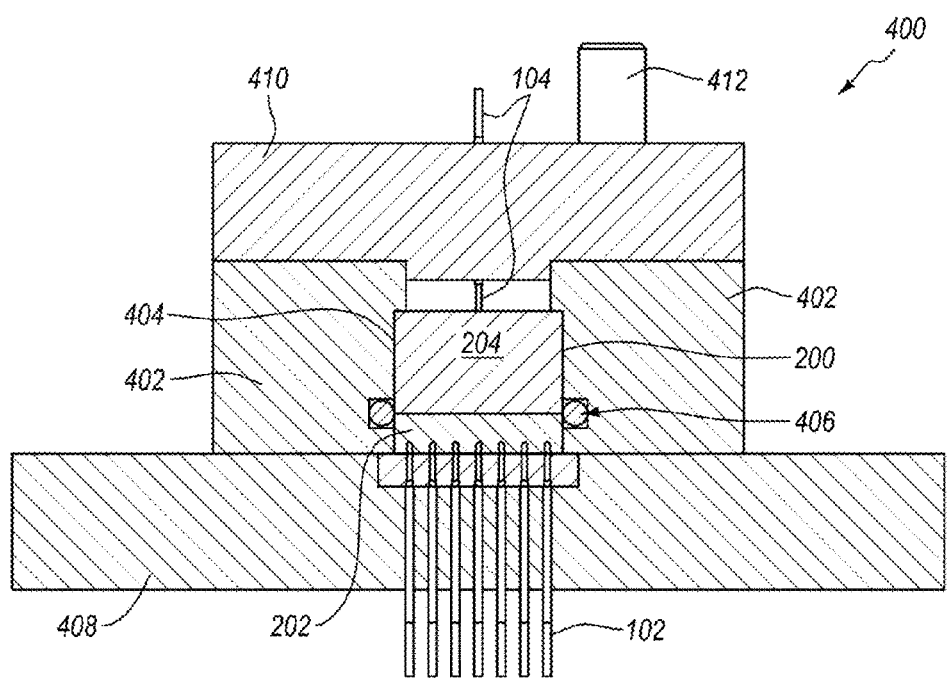
FIG. 4B is a cross-sectional view of the sample-holder assembly shown in FIG. 4A, with a PDC sample to be tested held therein.

FIGS. 4A and 4B illustrate an embodiment of a sample holder 400 that facilitates placement of the PDC sample 200 to be tested using the system 100 so that reliable electrical contact with the sensor probes 102 and 104 may be established. The main body 402 has a cavity 404 therein configured for holding the PDC sample 200. The PDC sample 200 may be centered and held in place by a resilient member 406 (e.g., a soft O-ring) that is disposed in a groove formed in the main body 402 that encircles the PDC sample 200 and defines part of the cavity 404. The resilient member 406 allows turning the part holder upside-down to place the part on top of the spring-loaded probes 102. The probes 102 are installed in and project outwardly from a base 408 having corresponding holes (e.g., 121 holes) drilled therein. The sensor assembly 400 may include a cap 410 that carries the reference probes 104 (only one is shown in FIG. 4B and two reference probes are included in this embodiment) that contact the substrate 204 of the PDC sample 200. One or more dowel pins 412 or other alignment structure may extend through sample holder components 402, 408, and 410 to keep them in alignment. Referring specifically to FIG. 4A, the components of the sample holder 400 may be compressed together so that the probes 102 and 104 are in electrical contact with the PDC sample 200 by, for example, thumb screws 414 or other compression mechanism. The cap 410, main body 402, and base 408 may be made from a number of different plastics.

Poor probe contact with the PCD table 202 of the PDC sample 200 may occur due to diamond crystals protruding from and/or forming a portion of the upper surface 203 of the PCD table 202, which may prevent or limit the probe from making sufficient contact with the metal-solvent catalyst (e.g., cobalt) in the PCD table 202 in the interstitial regions between the bonded diamond crystals. In an embodiment, a conductive grease (e.g., a conductive grease containing silver, copper, gold, or combinations thereof) may be applied to the surface 203 of the PCD table 202 to help reduce the occurrence of poor probe contact. Depending upon the PCD table surface quality and/or type of conductive grease, the probe electrical contact may be intermittent, with contact resistance varying over time, sometimes quickly and erratically.

Three techniques may be used to reject bad data caused by such poor probe contact. First, the probe contact resistances are measured under full drive current by setting the current and voltage multiplexers to the same address and the amplifier to unity gain. Probes exhibiting resistance over a selected threshold (typically 100Ω at 50 mA drive) are not used for measurements, resulting in the expulsion of several probe pairs from the measurement list.

Second, for each probe pair in the measurement list, two measurements are made: probe #1 current/probe #2 voltage and probe #2 current/probe #1 voltage. Reciprocity dictates that the results of these two measurements should be the same. If the measurements differ by a predetermined amount (typically 20%), the measurement from this probe pair is rejected. Otherwise, the two measurements are averaged to produce the resistance value recorded in the dataset.

The third technique for data rejection is centered on the DC offset in the measurement chain. Although no attempt is made to null the offset in the analog chain, it is still relatively low under normal circumstances. Offset is measured by performing the same measurement with positive and negative drive current, and averaging the results. If the measured offset is larger in magnitude than a preset threshold (typically 4 times the normal offset), the measurement from this probe pair is rejected. Otherwise, the measurements with positive and negative current are subtracted, thereby eliminating the offset from the measurement. Performing the positive/negative current measurements in rapid succession also helps filter out 1/f noise in the analog chain, providing nearly the same benefit as low-frequency AC measurements commonly used with EIT. The only drawback is the slowdown caused by the need to wait out the settling time of the current source twice for each measurement.

The input to the data acquisition routine is a list of probe pairs where measurements are to be performed. In an embodiment, probe pairs may not be repeated with probe order reversed unless reciprocal measurements are made to verify probe pair integrity. The reference probes contacting the substrate 204 of the PDC sample 200 being tested are not multiplexed in this embodiment, and therefore are not included in the measurement list. The output of the data acquisition routine is a list containing a resistance measurement for each probe pair. The number of output measurements may be lower than the number of input probe pairs due to some measurements being rejected. The reconstruction algorithm may still process the data, but localized loss of resolution can be expected.

The reconstruction algorithms for EIT have been thoroughly described elsewhere in Loke M H and Barker R D 1996 Rapid least-squares inversion of apparent resistivity pseudosections by a quasi-Newton method *Geophysical Prospecting* 44 131-52; Pain C C, Herwanger J V, Worthington M H and de Oliveira C R E 2002 Effective multidimensional resistivity inversion using finite-element techniques *Geophys. J. Int.* 151 710-28; Borcea L 2002 Electrical impedance tomography Inverse Problems 18 R99-R136; Loke M H 2004 *Tutorial: 2-D and 3-D electrical imaging surveys* Online: http://www.geoelectrical.com/coursenotes.zip (Accessed: May 5, 2008); Lionheart W R B 2004 EIT reconstruction algorithms: pitfalls, challenges and recent developments *Physiol. Meas.* 25 125-42; and Adler A and Lionheart W R B 2006 Uses and abuses of EIDORS: an extensible software base for EIT *Physiol. Meas.* 27 S25-S42, the disclosure of each of which is incorporated herein, in its entirety, by this reference.

In an embodiment, the reconstruction software utilized by the computer 120 (FIG. 1) of the system 100 to reconstruct the electrical conductivity distribution may be based on an FEM forward solver and an iterative least squares inverse solver. A tetrahedral mesh, such as the one shown in FIG. 5, may be used to represent both the electric potential and the electrical conductivity distribution. The interpolation for both quantities is linear so that the number of unknowns is equal to the number of nodes in the mesh (4426 in the mesh of shown FIG. 5). Linear interpolation may be chosen for the electrical conductivity distribution to reduce the number of unknowns compared to the more typical piecewise constant electrical conductivity representation. Linear interpolation also allows a natural implementation of a smoothness criterion. Optionally, the electrical conductivity distribution may be assumed to be isotropic.

Figure 5:
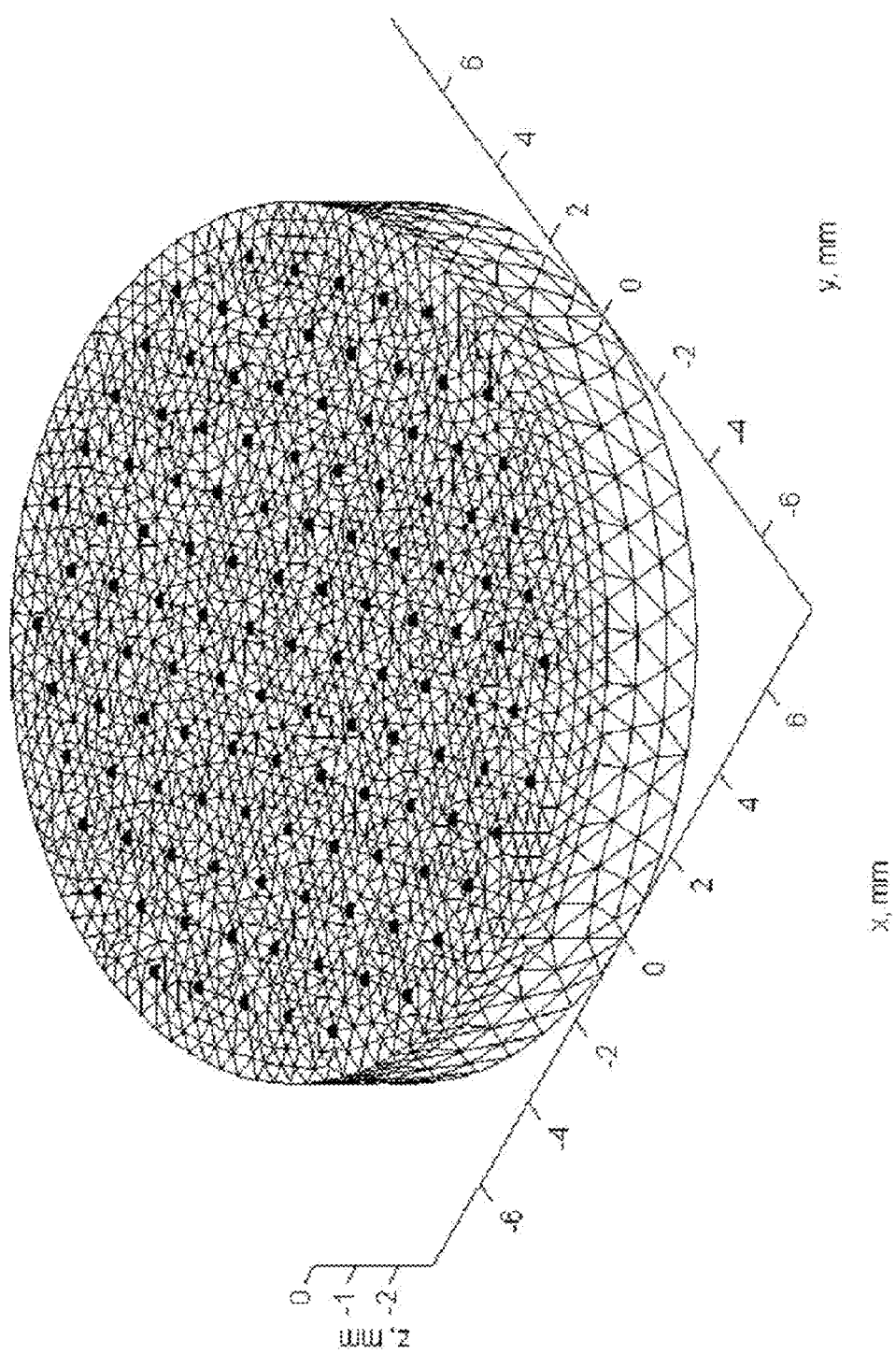
FIG. 5 is an embodiment of a finite element model ("FEM") mesh used for electrical conductivity reconstruction.

The mesh in FIG. 5 only covers the PCD table 202 of the PDC sample 200. The substrate 204 may be modeled as a perfect ground plane. The spring-loaded probe contact points 102' are highlighted with black dots. The mesh density decreases with depth to reduce computational complexity. This is acceptable because the resolution of the electrical conductivity imaging method naturally decreases with depth, and the requirements for accurate electric potential representation also reduce with distance away from the current injection probes. The reconstruction process may benefit from a higher mesh density for electric potential compared to electrical conductivity. Rather than using two separate meshes, in an embodiment, one solution may employ a higher-order interpolation for electric potential, but this is yet to be implemented in the custom solver.

The inverse problem amounts to the minimization of the following objective function:

$$F = (R_{meas} - R)^T W (R_{meas} - R) + \lambda \sigma^T S \sigma \tag{1}$$

The first term in (1) minimizes the residuals, the difference between the measured resistances $R_{meas}$ and the FEM simulated resistances R. The weighing matrix W is the inverse of the covariance matrix of the resistance measurements, and is typically diagonal, assuming the noise in the measurements is uncorrelated (which is an approximation):

$$W_{ii} = \frac{1}{\mathrm{var}(R_{meas_i})} = \frac{1}{(stdev(R_{meas_i}))^2} \tag{2}$$

The second term in (1) is the smoothness criterion on the discretized electrical conductivity distribution σ. It minimizes the spatial derivatives of the electrical conductivity distribution. For the S matrix, the discretized version of the differential $\nabla^2$ operator is adopted, which naturally emerges from the FEM formulation. The scalar parameter λ controls the trade-off between data fit and solution smoothness.

The reconstruction process starts with an initial guess resulting from assuming the electrical conductivity distribution is homogeneous. Each subsequent estimate of the electrical conductivity distribution is obtained as follows:

$$\sigma_{k+1} = \sigma_k + \Delta \sigma \tag{3}$$

where k is the iteration number, and Δσ is determined by solving $$(J^T W J + \lambda S) \Delta \sigma = J^T W (R_{meas} - R_k) - \lambda S \sigma_k \tag{4}$$

where $J_{ij} = \partial R_i / \partial \sigma_j$ is the Jacobian matrix. The expression (4) directly results from setting the gradient of the objective function (1) to zero after linearizing the relationship between R and $\sigma = \sigma_{k+1}$ as $R = R_k + J \Delta \sigma$. Convergence improves if (4) is formulated in terms of log(σ) instead of σ, since this keeps σ positive and works over a wide a dynamic range, but does not significantly distort the smoothness criterion. The computation of the Jacobian matrix is covered in the literature, for example in the article Lionheart W R B 2004 EIT reconstruction algorithms: pitfalls, challenges and recent developments *Physiol. Meas.* 25 125-42, which is incorporated herein, in its entirety, by this reference. It requires the solution of the forward FEM problem for the same number of excitations as there are probes.

Regarding the trade-off between the smoothness and data fit, adjusting the value of $\lambda$ may be desirable during the iteration process. If the standard deviations of the resistance data are known or assumed, $\lambda$ should be selected such that the residuals $R_{meas}-R$ on average replicate the expected deviations from the measured values:

$$\frac{(R_{meas} - R)^T W (R_{meas} - R)}{N_{meas}} = \frac{1}{N_{meas}} \sum_{i=1}^{N_{meas}} \frac{(R_{meas_i} - R_i)^2}{(stdev(R_{meas_i}))^2} \approx 1 \quad (5)$$

where $N_{meas}$ is the number of four-probe resistance measurements. The value of $\lambda$ that satisfies (5) is unknown a priori. In an embodiment, one way to converge on the appropriate value is to iteratively adjust $\lambda$ as follows:

$$\lambda_{k+1} = \lambda_k \frac{N_{meas}}{(R_{meas} - R_k)^T W (R_{meas} - R_k)} \quad (6)$$

Even adjusting 2 during the iteration process, only about 4-7 iterations are typically needed to converge on a solution where the residuals closely replicate the expected noise in the measurements. The runtime is on the order of 5 minutes for a single-threaded implementation, bottlenecked by the solution of (4).

Since the actual standard deviations for the resistance measurements are difficult to determine, approximations are constructed as follows:

$$stdev(R_{meas_i}) = aR_{meas_i} + b \quad (7)$$

where a specifies the relative variation and b the absolute variation. Generally, it is found that the relative variation is dominant, with a variety of sources (e.g. probe positioning errors, FEM numerical inaccuracy), while absolute variation is due to electrical noise alone. In practice, a 5% standard deviation (a=0.05) produces a smooth electrical conductivity distribution. Slightly lower values (down to 3%) improve resolution at the expense of some noise in the electrical conductivity distribution.

III. Test Results

Figure 6A:
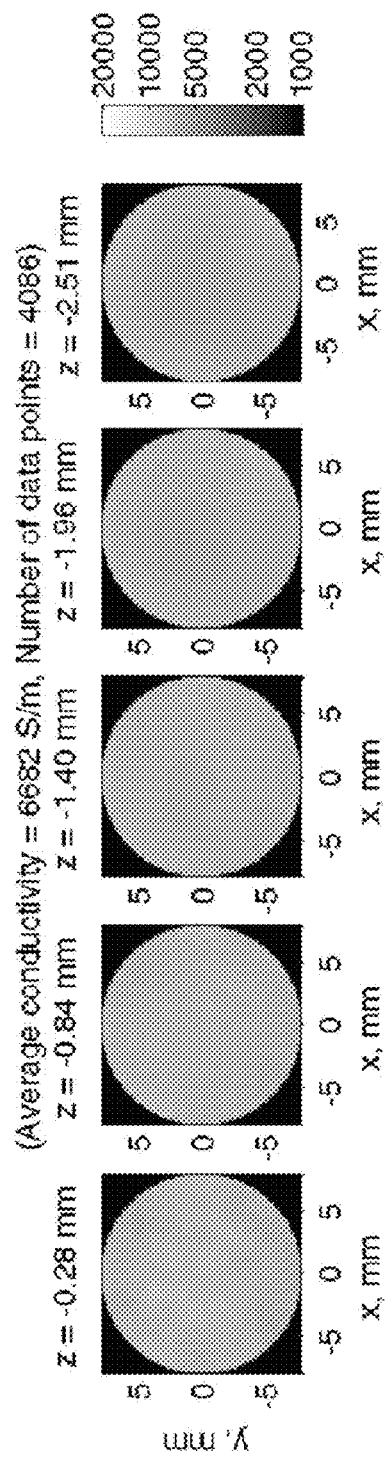
FIGS. 6A and 6B are electrical conductivity distributions in PCD tables of two different PDC cutter samples having relatively homogenous electrical conductivity distributions, with the electrical conductivity grey scale in Siemens/meter ("S/m").
Figure 6B:
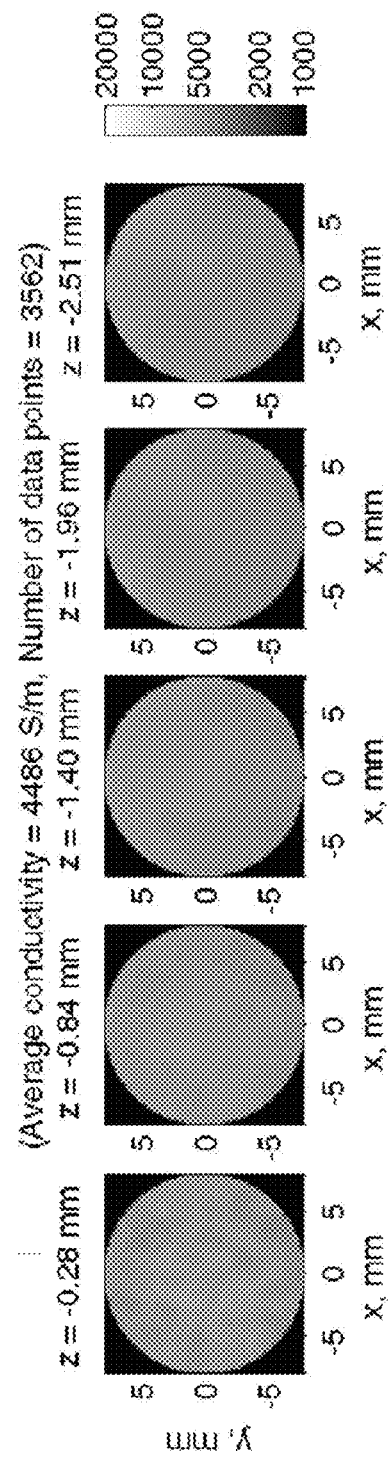

The described system 100 was used to test a variety of PDC cutter samples. Each PDC cutter sample included a cobalt-cemented carbide substrate having a PCD table bonded thereto. The PCD tables are comprised of a plurality of bonded-together diamond crystals having cobalt infiltrated from the substrate and disposed interstitially between the bonded-together diamond crystals. A typical "good" cutter is expected to have a substantially homogeneous PCD table, and this is typically reflected in electrical conductivity images after collecting data on more than 100 cutters. The electrical conductivity distributions of PCD tables from two PDC cutters having substantially homogeneous PCD tables are shown in FIGS. 6A and 6B. The electrical conductivity was reconstructed assuming a 3% standard deviation for the data. Five slices through the 3D electrical conductivity distribution are shown at varying depths into the PCD table measured from an upper surface of the PCD table (e.g., the upper surface 203 in FIG. 1). The depth is indicated above each slice. Even though the electrical conductivity is substantially homogeneous, the average electrical conductivity varied from sample to sample, and was found to be strongly influenced by metal-solvent catalyst content.

Figure 7A:
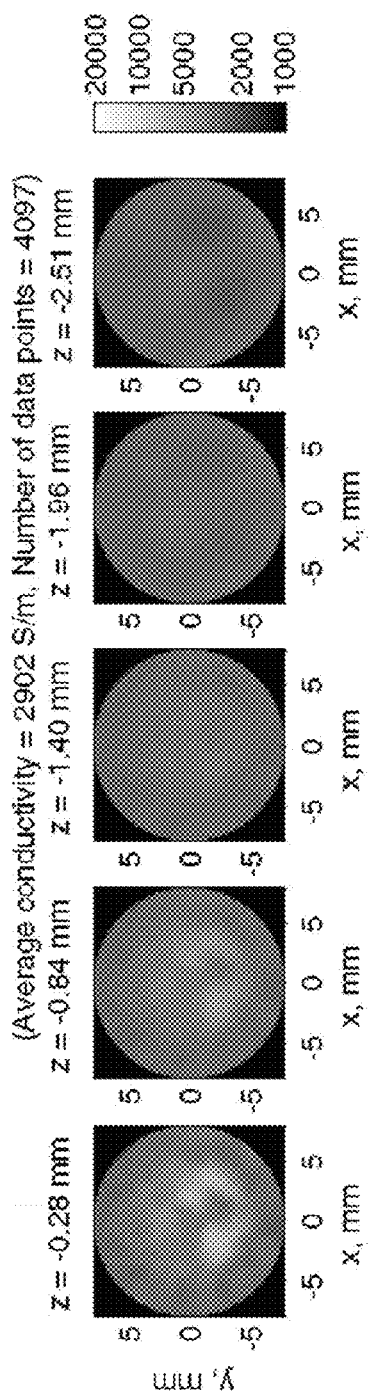
FIGS. 7A and 7B are electrical conductivity distributions in PCD tables of two different PDC cutter samples having poor sinter spots.
Figure 7B:
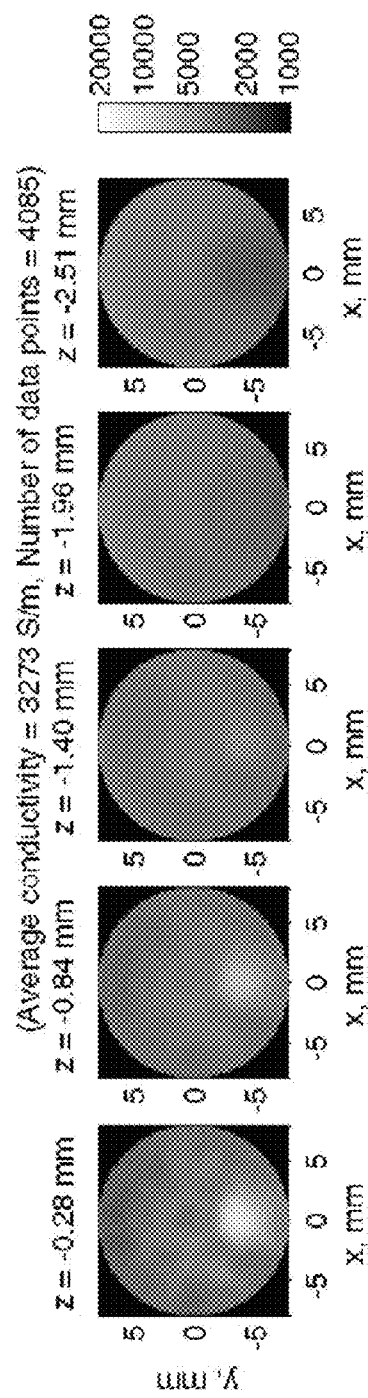

FIGS. 7A and 7B shows inhomogeneous electrical conductivity images obtained from two different PDC cutter samples that had surface-breaking poorly sintered regions visible at the upper surface of the PCD table. The poorly sintered regions were apparent as high-electrical-conductivity zones (i.e., bright zones), although not all poorly sintered regions detected visually were visible in the electrical conductivity images.

Figure 8A:
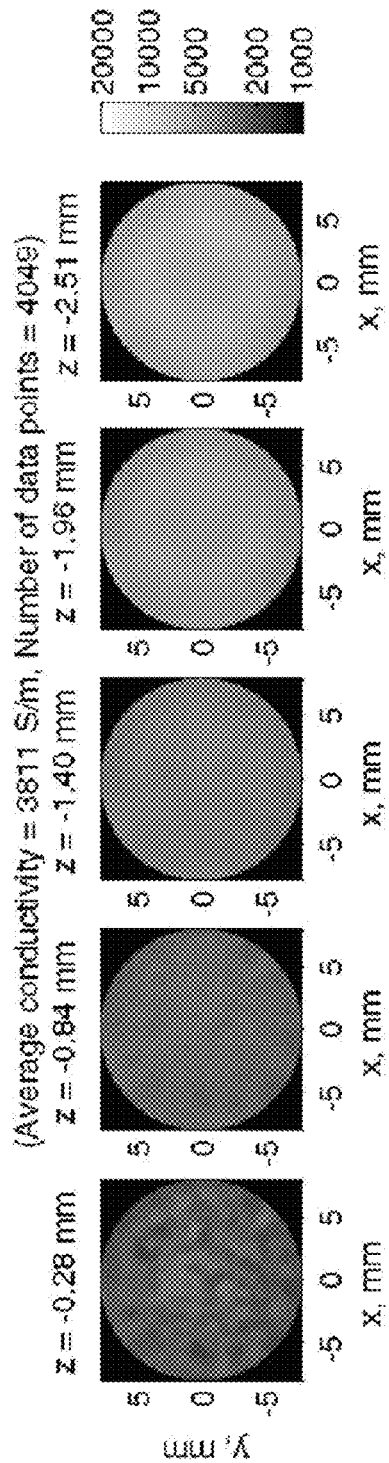
FIGS. 8A and 8B are electrical conductivity images from two different PDC cutter samples each having a patterned interface between the PCD table and the substrate.
Figure 8B:
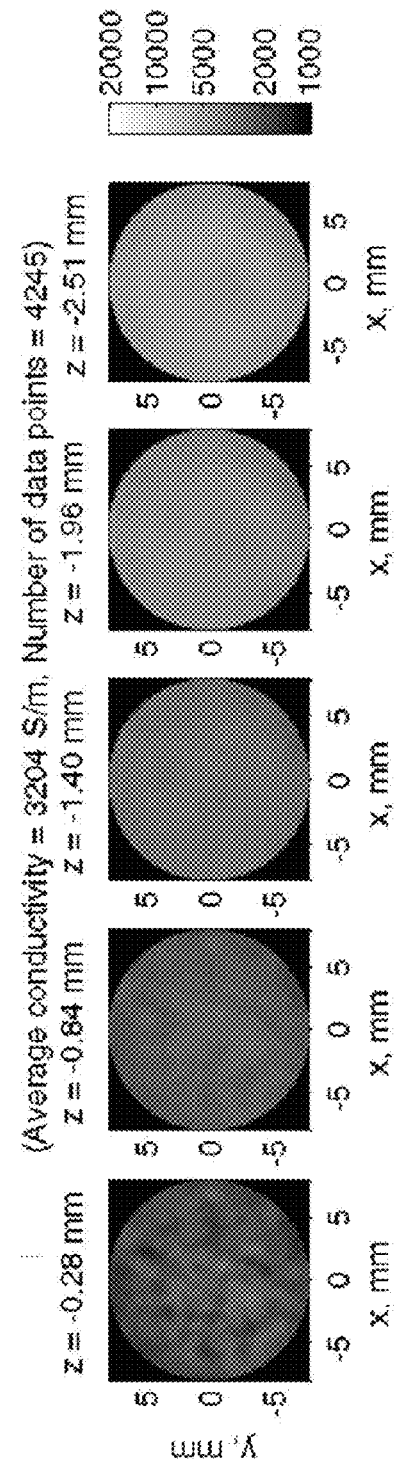

FIGS. 8A and 8B shows electrical conductivity images from two different PDC cutter samples with a patterned rather than a flat interface between the diamond table and the substrate. The details of the interface pattern are not resolved. Instead, the electrical conductivity gradually increased with depth.

FIGS. 9A and 9B shows electrical conductivity images from PDC cutter samples having ring-like low-electrical-conductivity features that are believed to have resulted from poor metal-solvent catalyst penetration into the PCD table. These narrow, high-contrast features make it difficult to converge on a solution that satisfies the expected data standard deviation. An additional impediment is that several probes directly over the low-electrical-conductivity features did not make good contact due to lack of metal-solvent catalyst and, therefore, were excluded from the dataset.

Figure 10A:
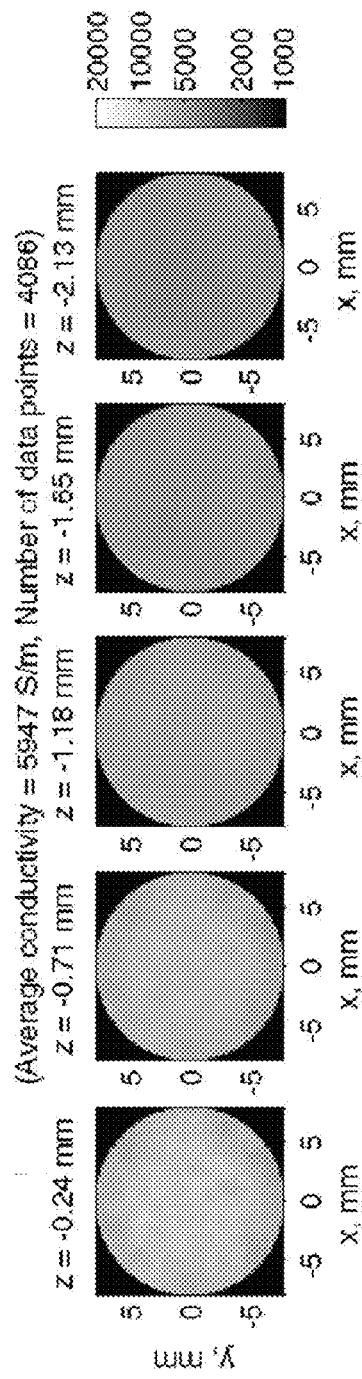
FIGS. 10A and 10B are examples of image inhomogeneity artifacts resulting from using a shallower FEM mesh.
Figure 10B:
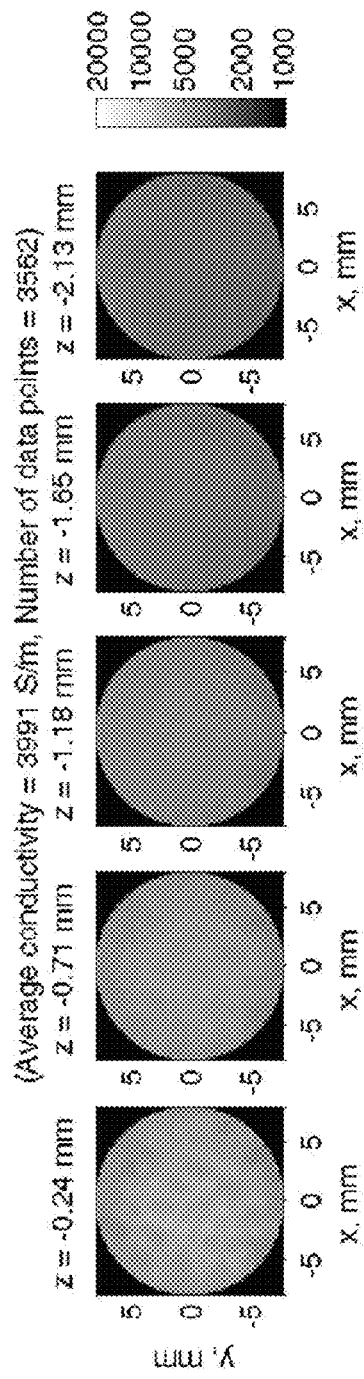

While conducting electrical conductivity imaging experiments on the PDC cutter samples, it was found that the reconstructed electrical conductivity tends to decrease with depth and towards the edges of the PCD table in most samples, even though homogeneous electrical conductivity is expected. FIGS. 10A and 10B shows examples of this effect, where a mesh conforming to the measured diamond table thickness was used. The electrical conductivity images in FIG. 10A were generated using a higher-resolution mesh than used to generate the electrical conductivity images shown in FIG. 10B. Synthetic data from a higher-resolution mesh (FIG. 10A) has ruled out FEM numerical inaccuracy as a contributor to this artifact. One possible contribution seems to be the fact that the substrate is not a perfect conductor, and incurs some voltage drop. The resistance of the substrate is expected to add a small, nearly constant bias to each measurement. As a result, this effect should be more prominent in higher electrical-conductivity samples, where the measured resistances are low, and the relative contribution of the substrate is greater. However, this is not what is observed in practice. Low electrical-conductivity samples seem to be affected to the same degree. Optionally, a temporary solution to remove this effect is to slightly increase the thickness of the PCD table mesh used for reconstruction. Although this slightly distorts the depth and average electrical conductivity information, homogeneous images can be obtained. The images in FIGS. 6A and 6B are from same datasets as in FIGS. 10A and 10B, but reconstructed on an 18% thicker mesh. An alternative explanation is that the nature of the HPHT sintering of the PCD table (e.g., greater than 7 GPa) and/or sintering constituents may cause the electrical conductivity to be lower and generate this effect.

Figure 11:
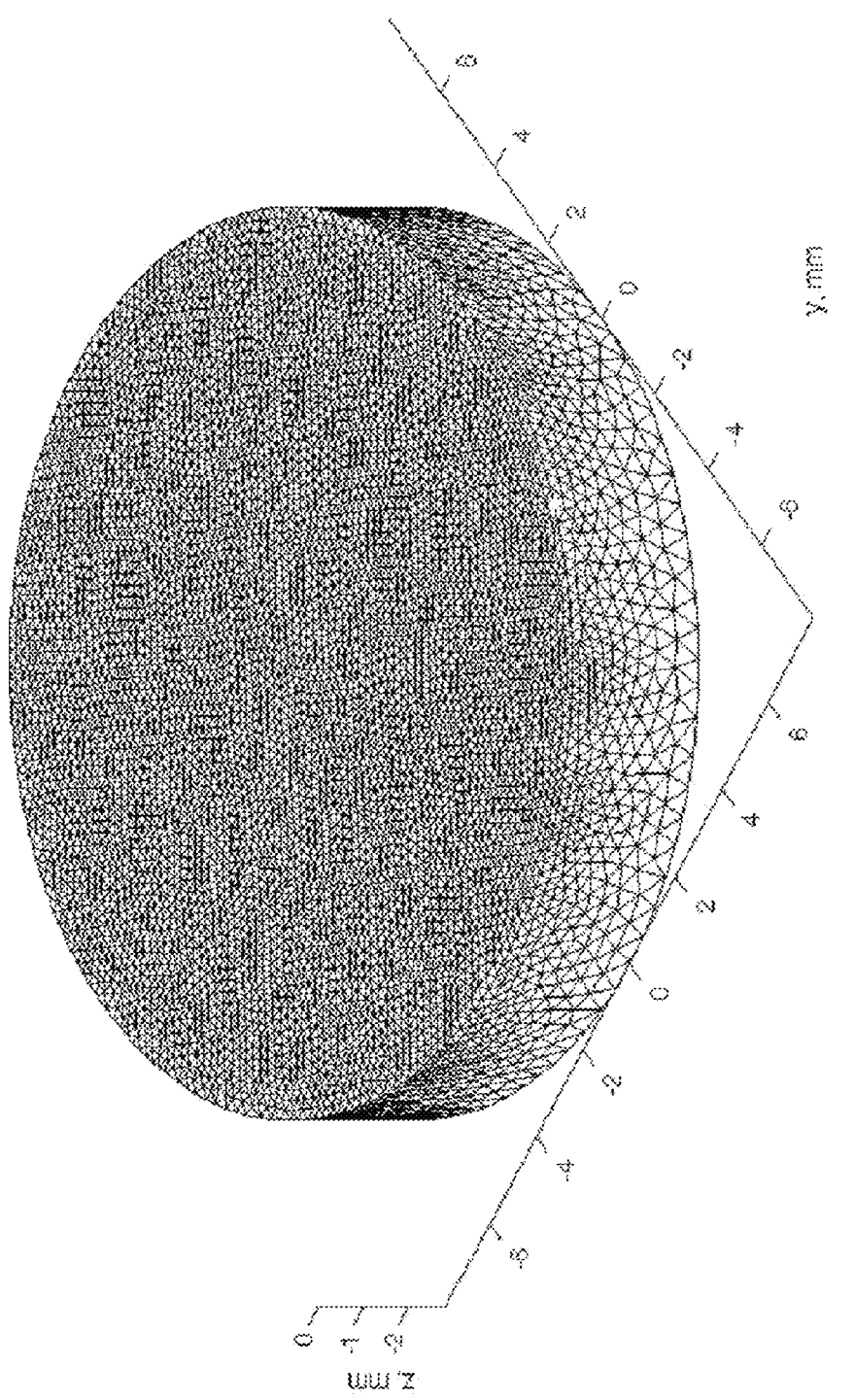
FIG. 11 is an FEM mesh used to generate synthetic data.
Figure 12A:
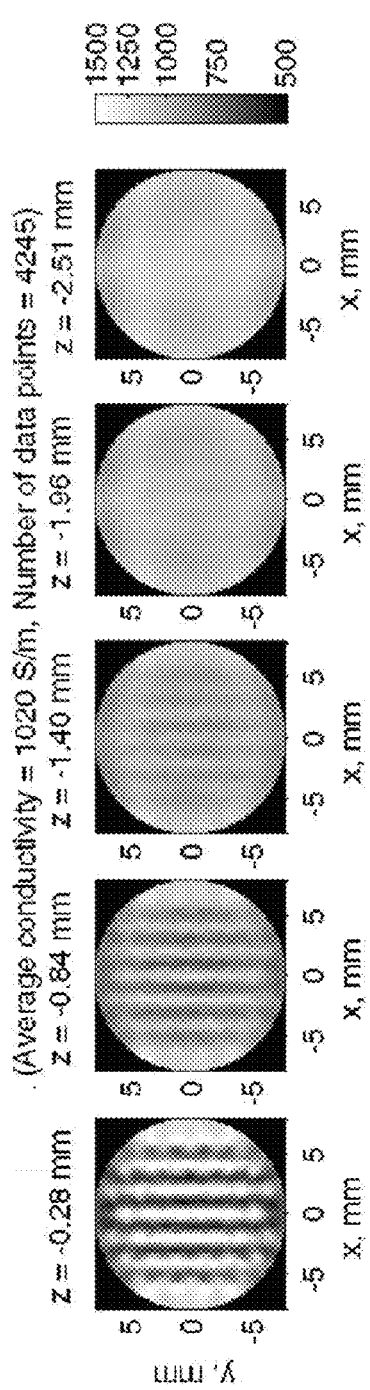
FIGS. 12A-12D are electrical conductivity imaging resolution tests using synthetic data at a 2 mm period, 2.8 mm period, 4 mm period, and 5.7 mm period, respectively.
Figure 12B:
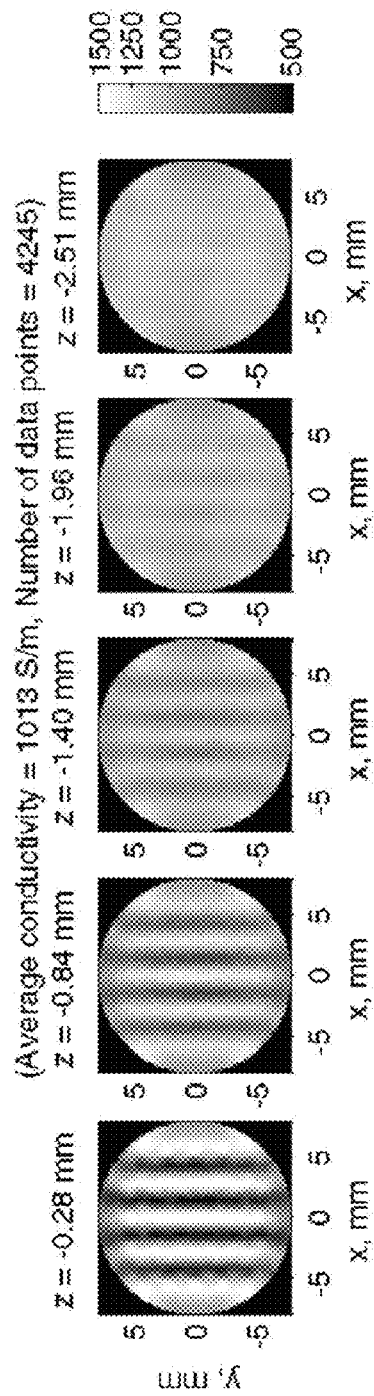
Figure 12C:
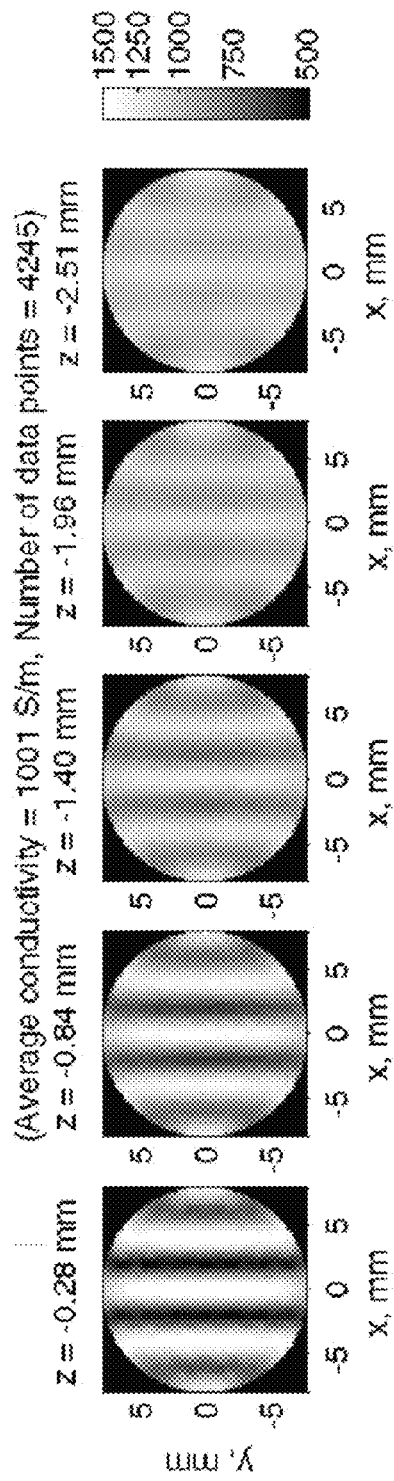
Figure 12D:
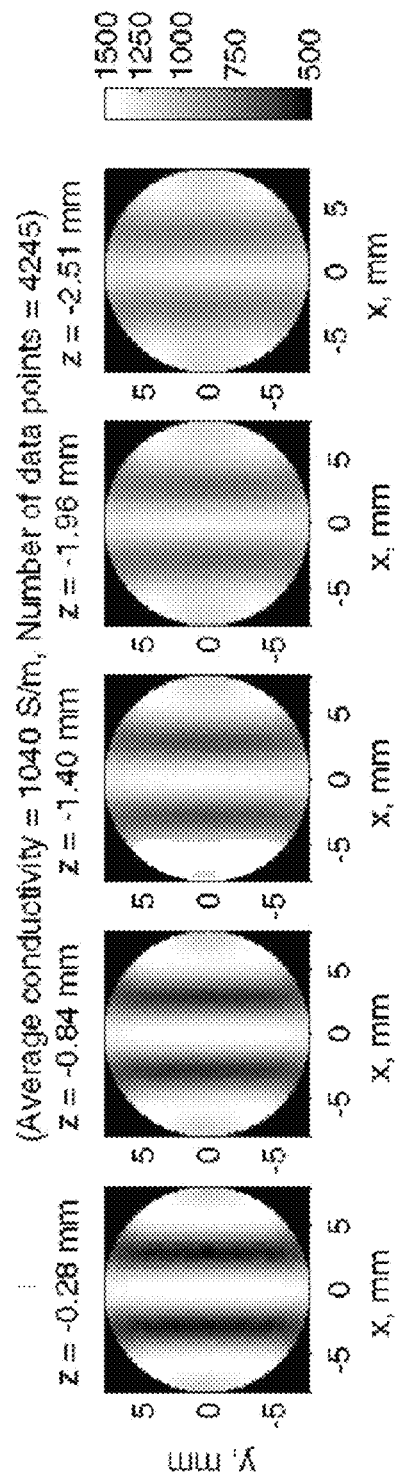

To study the imaging resolution of the system 100, synthetic data was generated using the higher-resolution mesh in FIG. 11 (44,540 nodes). The synthetic electrical conductivity distributions were sinusoidal with periods varying from 2.0 mm to 5.7 mm in multiples of √2. The variation was in the x-direction only. The synthetic electrical conductivity varied from 500 S/m to 1500 S/m (1000 S/m peak-to-though), a 3× difference, which is medium contrast for this method. For the reconstruction, a 4245-measurement dataset was used with an assumed 3% standard deviation for the resistance data. FIGS. 12A-12D plots the reconstructed electrical conductivity distributions from synthetic data. The effect of depth on resolution is apparent. If the imaging resolution is approximated as the half-period of the sinusoidal distribution where contrast decreases in half, the resolution near the surface is about 1 mm, while at mid depth it is 2 mm, and at maximum depth, it is about 3 mm.

It is possible to adjust the smoothness criterion to give less weight to electrical conductivity variation at depth. This has the effect of trading off resolution near the surface for resolution at depth. To illustrate this, FIG. 13A presents the reconstructed electrical conductivity from the same dataset as in FIG. 12C, where the smoothness criterion is weighted to decrease with depth according to FIG. 13B. Both a slight increase in resolution at depth and a slight decrease of resolution near the surface are observed. An overall decrease of resolution with depth is still unavoidable, since the dataset contains more information about the electrical conductivity near the surface. Heavily relaxing the smoothness constraint with depth will only result in noise dominating the images at depth. In some embodiments, a PCD table of a PDC sample may be lapped and/or ground and measurements may be repeated at different depths to verify and/or improve the model.

IV. Applications

Figure 14:
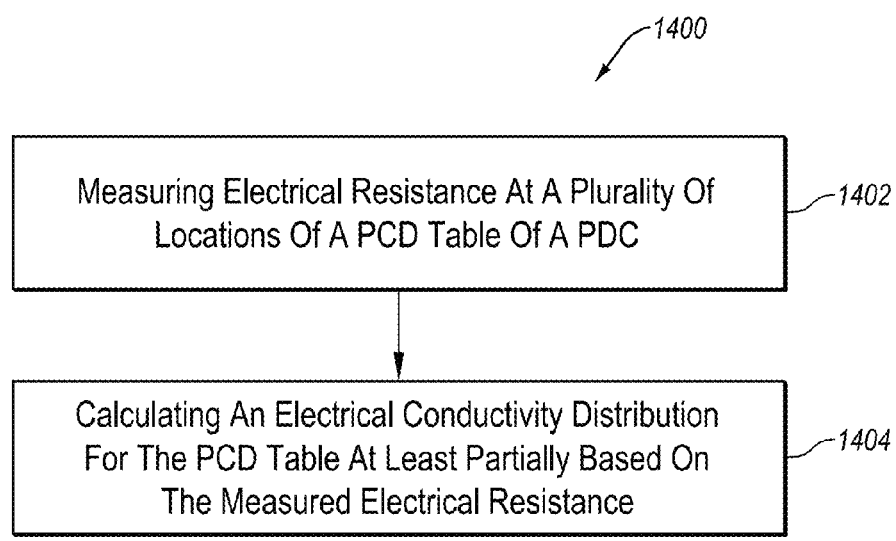
FIG. 14 is a flow diagram of a method of non-destructively testing a PCD table of a PDC according an embodiment of a quality control method.

The system 100 may be employed in various different applications in the manufacture of PDCs and rotary drill bits. In an embodiment, the system 100 may be used for quality control to determine whether a PDC meets certain manufacturer or end user requirements. FIG. 14 is a flow diagram of a method 1400 of non-destructively testing a PCD table of a PDC according an embodiment of a quality control method that may be implemented by the system 100 or another suitable system. The PDC may be a one-step or two-step PDC. For example, one or more PDCs may be tested using the system 100 to determine the electrical conductivity distribution of the PCD table of the PDC. The method 1400 includes an act 1402 of measuring an electrical resistance at a plurality of locations of the PCD table of the PDC. As discussed hereinabove, the plurality of locations may be surface locations on the upper surface of the PCD table. The method further includes an act 1404 of calculating an electrical conductivity distribution for the PCD table at least partially based on the measured electrical resistance. The calculation of the 3D electrical conductivity distribution of the PCD table may be performed using EIT techniques as discussed hereinabove.

Figure 15:
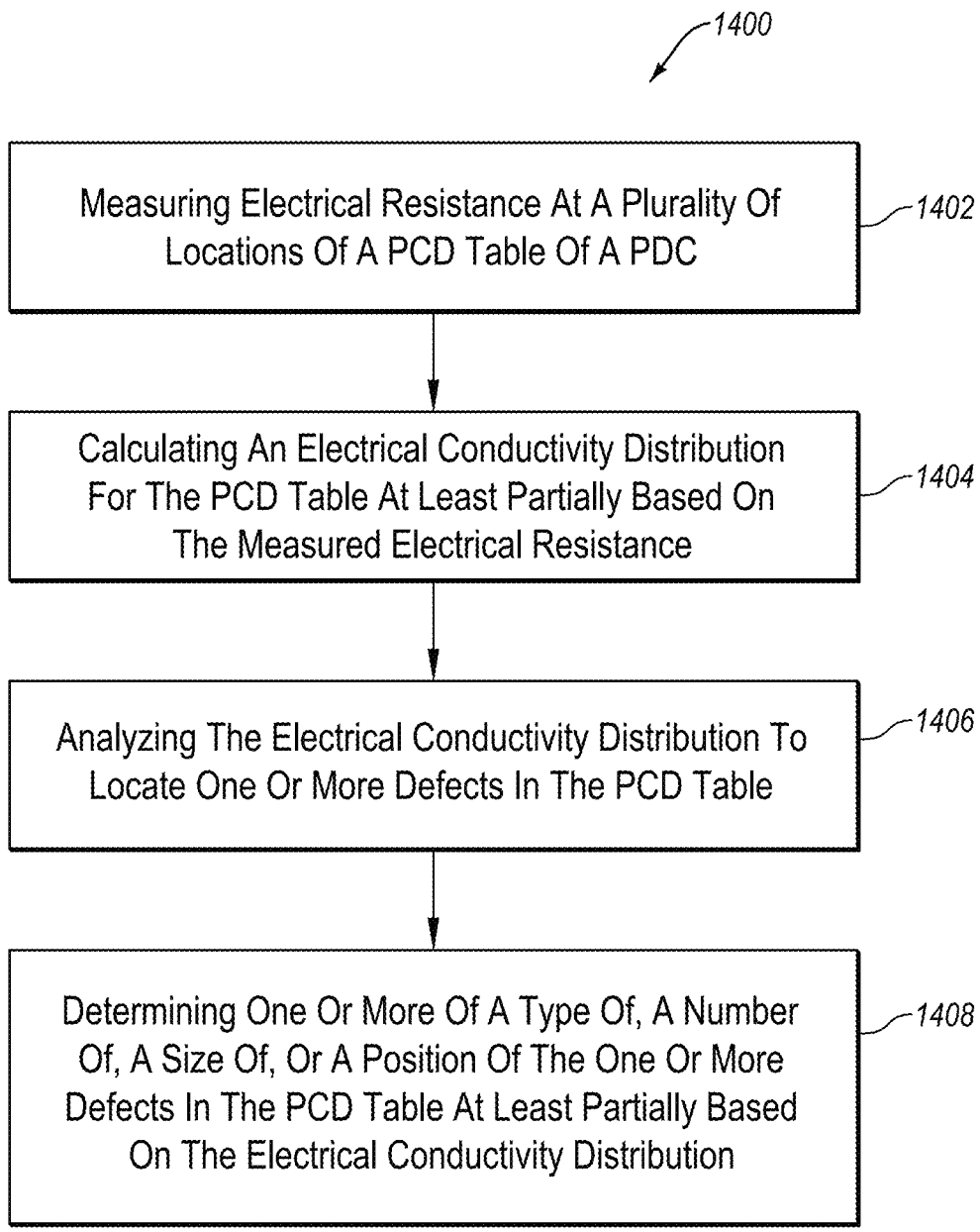
FIG. 15 is a flow diagram of a more detailed method of non-destructively testing a PCD table of a PDC according an embodiment of a quality control method

Referring to the flow chart in FIG. 15, the method 1400 may further include an act 1406 of analyzing the electrical conductivity distribution to determine if one or more defects (e.g., poorly sintered regions, cracks, porosity, or combinations thereof) are present in the PCD table. The analyzing may be performed by the software stored in the memory 121 of the computer 120, may be performed by an analyst, or both. The one or more defects may be identified as one or more high-electrical-conductivity regions and/or one or more low-electrical-conductivity regions in the PCD table at least partially based on the electrical conductivity distribution. When present, the one or more high-electrical-conductivity regions may exhibit any of the disclosed electrical conductivity values or range of values disclosed hereinabove. For example, the average electrical conductivity of the PCD table may be about 2500 S/m and the average electrical conductivity of the one or more high-electrical-conductivity regions may be about 4000 S/m, the average electrical conductivity of the PCD table may be about 3000 S/m to about 5000 S/m and the average electrical conductivity of the one or more high-electrical-conductivity regions may be about 4500 S/m to about 9000 S/m, or the average electrical conductivity of the PCD table may be about 4000 S/m to about 4500 S/m and the average electrical conductivity of the one or more high-electrical-conductivity regions may be about 10000 S/m to about 15000 S/m. The method 1400 may additionally include an act 1408 of determining the type of, the number of the one or more defects, the size of each of the one or more defects, the position of each of the one or more defects, any combination of the foregoing properties, or another property. The determining may be performed by the software stored in the memory 121 of the computer 120, by the analyst, or both.

The PDC may be accepted or rejected based on some criteria regarding acceptable defects, such as defects having an acceptable size, number, location, or combinations of the foregoing properties. The acceptance or rejection may be automatically performed by the software stored in the memory 121 of the computer 120. For example, such one or more high-electrical-conductivity regions exhibit an electrical conductivity greater than an average electrical conductivity of the PCD table and may further exhibit the size, electrical conductivity, and relative electrical conductivity compared to average conductivity of the PCD table disclosed hereinabove.

The same basic methodology may be employed to adjust a manufacturing process. For example, a PDC may be formed by a first process and measured using the method 1400 shown in FIG. 15. The first process may be adjusted based on the measurements to generate a second process which may be used to manufacture one or more second PDCs. For example, the second process may be designed so that the one or more defects generated in the PCD table in the first process are not present in the PDCs manufactured according to the second process.

In other embodiments, the method 1400 may also be used to inspect a PCD element (i.e., a freestanding PCD table), such as an un-leached or partially leached PCD table after fabrication and prior to re-attachment to a substrate. In such a method, the acts 1402, 1404, 1406, and 1408 are modified so that the inspection acts are performed on a PCD element without a substrate (e.g., an un-leached or partially leached PCD table) as opposed to a PCD table of a one-step or two-step PDC and the calculation/analyzing acts is performed on the data for the freestanding PCD table.

After inspecting the PCD element, provided that the inspected PCD element passes quality control, the PCD element may be leached, if necessary or desired, and bonded to a substrate in a subsequent HPHT process. After inspecting the PCD element, the process used to fabricate the PCD element may also be altered in order to adjust and/or improve subsequently fabricated PCD elements.

Figure 16:
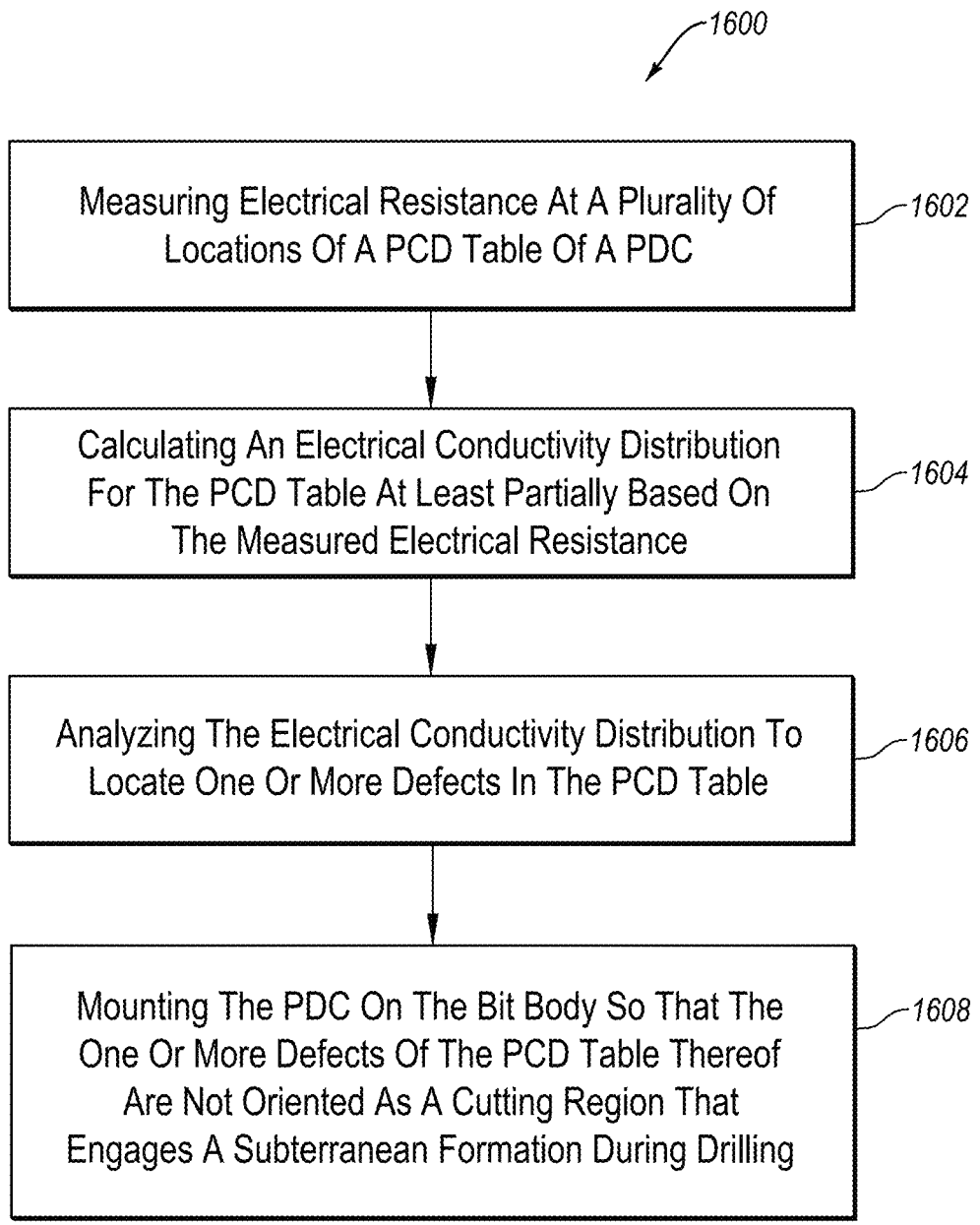
FIG. 16 is a flow diagram of a method of non-destructively testing and selectively orienting and mounting a PDC on a bit body of a rotary drill bit according an embodiment of a method.

FIG. 16 is a flow diagram of a method 1600 of non-destructively testing and selectively orienting and mounting a PDC on a bit body of a rotary drill bit according an embodiment of a method. For example, one or more PDCs may be tested using the system 100 to determine the electrical conductivity distribution of the PCD table of the PDC. The method 1600 includes an act 1602 of measuring an electrical resistance at a plurality of locations of a PCD table of the PDC. The method further includes an act 1604 of calculating an electrical conductivity distribution for the PCD table at least partially based on the measured electrical resistance. The calculation of the electrical conductivity distribution may be performed using EIT techniques as discussed hereinabove. The method further includes an act 1606 of analyzing the electrical conductivity distribution to locate one or more defects in the PCD table. The acts 1602, 1604, and 1606 may be the same or similar to the acts 1402, 1404, and 1406 described with respect to the method 1400.

For example, when the one or more defects are one or more high-electrical-conductivity regions, the one or more high-electrical-conductivity regions exhibit an electrical conductivity greater than an average electrical conductivity of the PCD table and a maximum linear cross-sectional dimension of at least about 0.25 mm (e.g., about 0.5 mm to about 4 mm, about 1 mm to about 3 mm, about 1 mm to about 2 mm, or about 0.75 mm to about 1.75 mm). The one or more high-electrical-conductivity regions may exhibit any of the disclosed electrical conductivity values or range of values disclosed hereinabove. For example, the average electrical conductivity of the entire PCD table may be about 2,500 S/m and the average electrical conductivity of the one or more high-electrical-conductivity regions may be about 4,000 S/m, the average electrical conductivity of the entire PCD table may be about 3,000 S/m to about 5,000 S/m and the average electrical conductivity of the one or more high-electrical-conductivity regions may be about 4,500 S/m to about 9,000 S/m, or the average electrical conductivity of the entire PCD table may be about 4,000 S/m to about 4,500 S/m and the average electrical conductivity of the one or more high-electrical-conductivity regions may be about 10,000 S/m to about 15,000 S/m.

The method 1600 additionally includes an act 1608 of mounting the PDC on the bit body of the rotary drill bit so that the one or more defects (e.g., the one or more high-electrical-conductivity regions and/or one or more low-electrical-conductivity regions) of the PCD table thereof are not oriented as a cutting region that engages a subterranean formation during drilling. For example, the mounting may be accomplished by press-fitting or brazing the selectively oriented PDC in a cutter pocket or recess of the bit body, such as a rotary drill bit body having fixed cutters. In such an embodiment, the leading edge or working region of the PCD table of the selectively oriented PDC may be substantially free of the one or more defects. For example, such one or more high-electrical-conductivity regions exhibit an electrical conductivity greater than an average electrical conductivity of the PCD table and may further exhibit the size, electrical conductivity, and relative electrical conductivity compared to average conductivity of the PCD table disclosed hereinabove.

Figure 17:
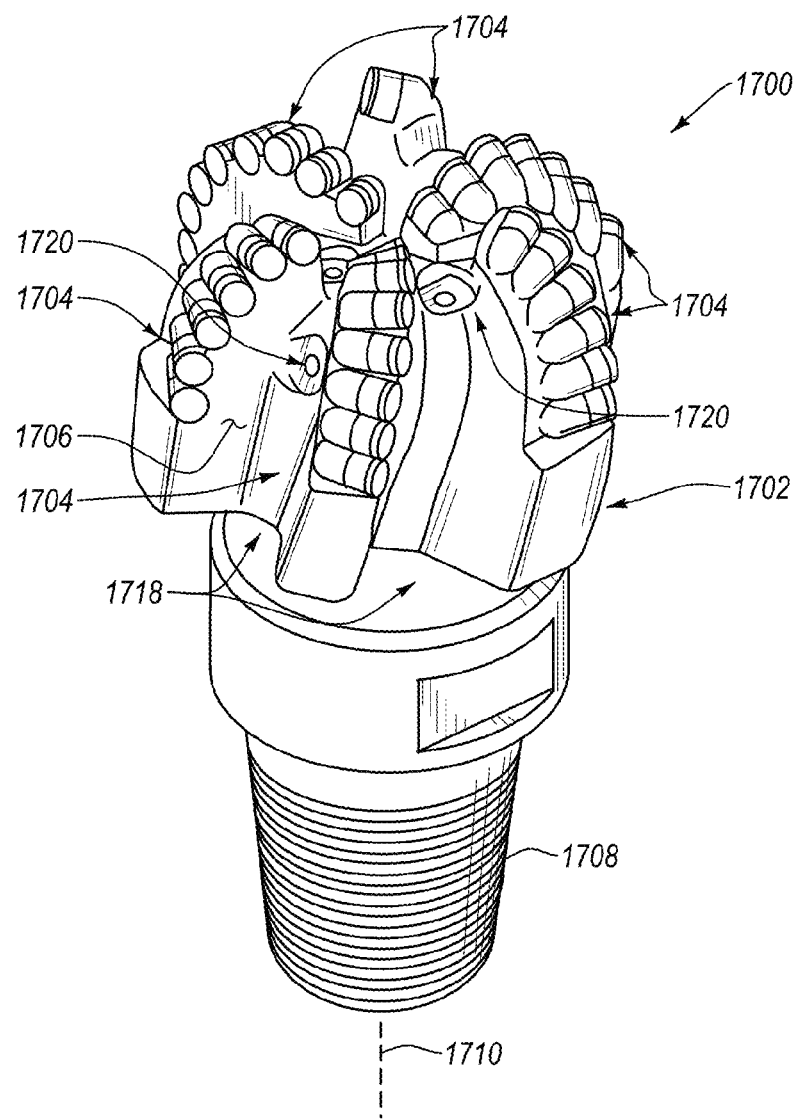
FIG. 17 is an isometric view of an embodiment of a rotary drill bit that may employ one or more of the PDC that were non-destructively tested using the systems and methods disclosed herein and selectively oriented and mounted on the bit body.
Figure 18:
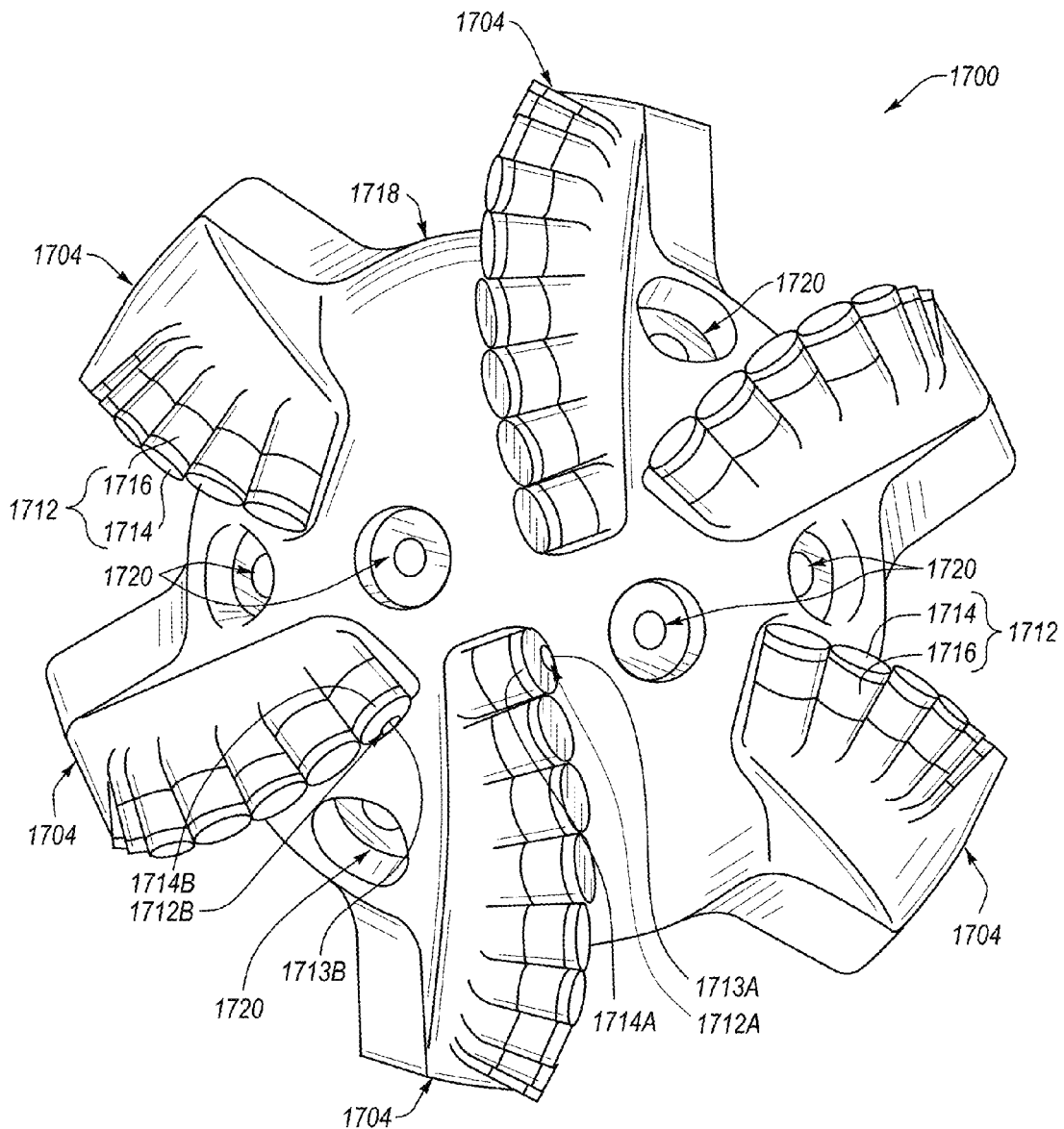
FIG. 18 is a top elevation view of the rotary drill bit shown in FIG. 17.

Referring to FIGS. 17 and 18, thus, in an embodiment, a rotary drill bit 1700 is disclosed that includes at least one PDC that is selectively oriented so that the one or more high-electrical-conductivity regions thereof identified using the non-destructive testing systems and methods disclosed herein are not positioned to engage a subterranean formation during drilling operations. The rotary drill bit 1700 comprises a bit body 1702 that includes radially and longitudinally extending blades 1704 having leading faces 1706, and a threaded pin connection 1708 for connecting the bit body 1702 to a drilling string. The bit body 1702 defines a leading end structure for drilling into a subterranean formation by rotation about a longitudinal axis 1710 and application of weight-on-bit. At least one PDC is selectively oriented so that the one or more high-electrical-conductivity regions thereof are not positioned to engage a subterranean formation during drilling operations may be affixed to the bit body 1702. With reference to FIG. 18, each of a plurality of PDCs 1712 is secured to the blades 1704 of the bit body 1702 (FIG. 17). For example, each PDC 712 may be brazed or press-fit in a recess/cutter pocket of the blades 1704. Each PDC 1712 may include a PCD table 1714 bonded to a substrate 1716. Also, circumferentially adjacent blades 1704 define so-called junk slots 1718 therebetween. Additionally, the rotary drill bit 1700 includes a plurality of nozzle cavities 1720 for communicating drilling fluid from the interior of the rotary drill bit 1700 to the PDCs 1712.

The PDCs 1712A and 1712B include corresponding PCD tables 1714A and 1714B having corresponding defects 1713A and 1713B therein. For example, the defects 1713A, 1713B may comprise one or more high-electrical-conductivity regions (e.g., one or more poorly sintered regions) and/or one or more low-electrical-conductivity regions (e.g., cracks and/or porosity). Referring to FIG. 18, the PDCs 1712A and 1712B are mounted to a corresponding one of the blades 1704 so that the defects 1713A and 1713B thereof identified using the non-destructive testing systems and methods disclosed herein are not positioned as a cutting region that engages a subterranean formation during drilling operations. Instead, the defects 1713A and 1713B are located, for example, immediately adjacent to the bit body 1702.

FIGS. 17 and 18 merely depict one embodiment of a rotary drill bit that employs at least one PDC that is selectively oriented so that the one or more defects thereof identified using the non-destructive testing methods disclosed herein are not positioned to engage a subterranean formation during drilling operations, without limitation. The rotary drill bit 1700 is used to represent any number of earth-boring tools or drilling tools, including, for example, core bits, roller-cone bits, fixed-cutter bits, eccentric bits, bicenter bits, reamers, reamer wings, or any other downhole tool including superabrasive compacts, without limitation.

In another embodiment, the PDC may be selectively oriented on and attached to vertical turret lathe ("VTL") test fixture so that the one or more defects are not positioned to engage and cut a workpiece (e.g., a Barre granite workpiece). The VTL test may be used to comparatively determine the thermal stability and wear resistance of PCD tables of PDCs. In such an embodiment, the leading edge or working region of the PCD table of the selectively oriented PDC may be substantially free of the one or more defects, such as one or more high-electrical-conductivity regions (e.g., one or more poor sintered regions) and/or one or more low-electrical-conductivity regions (e.g., cracks and/or porosity). For example, such one or more defects may comprise high-electrical-conductivity regions exhibit an electrical conductivity greater than an average electrical conductivity of the PCD table and may further exhibit the size, electrical conductivity, and relative electrical conductivity compared to average conductivity of the PCD table disclosed hereinabove.

Thus, the system 100 and methods disclosed herein may improve the reliability of VTL test because the comparative testing will be performed on region of the PCD tables that do not have aforementioned defects, such as poorly sintered regions, porosity, cracks, or combinations of the foregoing defects.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. A method of non-destructively testing a polycrystalline diamond compact ("PDC") including a polycrystalline diamond table bonded to a substrate, the method comprising:
   with an electrical impedance tomography system, measuring electrical resistance at a plurality of locations of the PDC, wherein measuring the electrical resistance at the plurality of location of the PDC includes:
      contacting an upper surface of the polycrystalline diamond table of the PDC with a first plurality of probes; and
      contacting a surface of the substrate of the PDC with a second plurality of probes, wherein the number of probes in the first plurality of probes exceeds the number of probes in the second plurality of probes; and
   with one or more processors, calculating an electrical conductivity distribution for the polycrystalline diamond table at least partially based on the measured electrical resistance.

2. The method of claim 1 wherein measuring electrical resistance at a plurality of locations of the PDC comprises with the electrical impedance tomography system, measuring the electrical resistance of a plurality of surface locations on the upper surface of the polycrystalline diamond table.

3. The method of claim 1 wherein calculating an electrical conductivity distribution for the polycrystalline diamond table at least partially based on the measured electrical resistance comprises employing an electrical impedance tomography technique to calculate the electrical conductivity distribution.

4. The method of claim 1, further comprising analyzing the electrical conductivity distribution to locate one or more defects in the polycrystalline diamond table.

5. The method of claim 4 wherein the one or more defects comprise one or more high-electrical-conductivity regions, the one or more high-electrical-conductivity regions exhibit an electrical conductivity greater than an average electrical conductivity of the polycrystalline diamond table and a maximum linear cross-sectional dimension of at least about 0.25 mm.

6. The method of claim 4, further comprising identifying the one or more defects as one or more high-electrical conductivity regions, one or more low-electrical-conductivity regions, or combinations thereof.

7. The method of claim 4, further comprising identifying the one or more defects as one or more poorly sintered regions, cracks, porosity, or combinations thereof.

8. The method of claim 1, further comprising accepting or rejecting the PDC at least partially based on the electrical conductivity distribution.

9. The method of claim 1, further comprising determining one or more of a type of, a number of, a size of, or a position of the one or more defects in the polycrystalline diamond table at least partially based on the electrical conductivity distribution.

10. The method of claim 9 wherein the type of the one or more defects comprises one or more poorly sintered regions, porosity, cracks, or combinations thereof.

11. A method of non-destructively testing a polycrystalline diamond element, the method comprising:
   with an electrical impedance tomography system, measuring electrical resistance at a plurality of locations of the polycrystalline diamond elements;
   with one or more processors, calculating an electrical conductivity distribution for the polycrystalline diamond element at least partially based on the measured electrical resistance; and
   analyzing the electrical conductivity distribution to locate one or more defects in the polycrystalline diamond element, the one or more defects including one or more high-electrical-conductivity regions.

* * * * *